US011553960B2

(12) United States Patent
Bohm et al.

(10) Patent No.: US 11,553,960 B2
(45) Date of Patent: Jan. 17, 2023

(54) METHODS FOR TREATING PATIENTS WITH CATHETER-BASED RENAL NEUROMODULATION

(71) Applicant: Medtronic Ardian Luxembourg S.a.r.l., Luxembourg (LU)

(72) Inventors: Michael Bohm, Saarlan (DE); Felix Mahfoud, Saarlan (DE); Sandeep Brar, Dublin, CA (US); Douglas Hettrick, Andover, MN (US); Martin Fahy, Brooklyn, NY (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 623 days.

(21) Appl. No.: 16/524,782

(22) Filed: Jul. 29, 2019

(65) Prior Publication Data

US 2020/0038102 A1    Feb. 6, 2020

Related U.S. Application Data

(60) Provisional application No. 62/712,882, filed on Jul. 31, 2018.

(51) Int. Cl.
*A61B 18/14*    (2006.01)
*A61B 18/02*    (2006.01)
(Continued)

(52) U.S. Cl.
CPC .. *A61B 18/1492* (2013.01); *A61B 17/320068* (2013.01); *A61B 18/02* (2013.01);
(Continued)

(58) Field of Classification Search
CPC ................ A61B 18/1492; A61B 18/02; A61B 17/320068; A61B 2017/320069;
(Continued)

(56) References Cited

U.S. PATENT DOCUMENTS 6,978,174 B2    12/2005  Gelfand et al.
7,653,438 B2     1/2010  Deem et al.
(Continued)

FOREIGN PATENT DOCUMENTS

WO    2013030041 A2    3/2013
WO    2014023738 A2    2/2014
(Continued)

OTHER PUBLICATIONS

C Tsioufis et al., Drug-resistant hypertensive patients responding to multielectrode renal denervation exhibit improved heart rate dynamics and reduced arrythmia burden, 2014, Journal of Human Hypertension, 28, 587-593 (Year: 2014).*
(Continued)

*Primary Examiner* — Michael F Peffley
*Assistant Examiner* — Bo Ouyang
(74) *Attorney, Agent, or Firm* — Shumaker & Sieffert, P.A.

(57) ABSTRACT

Methods for treating hypertension and associated systems and methods are disclosed herein. One aspect of the present technology, for example, is directed to methods for therapeutic renal neuromodulation that partially inhibit sympathetic neural activity in renal nerves proximate a renal blood vessel of a human patient having a 24-hour heart rate at or above a median heart rate for a population of hypertensive patients. This reduction in sympathetic neural activity is expected to therapeutically treat one or more conditions associated with hypertension of the patient. Renal sympathetic nerve activity can be modulated, for example, using an intravascularly positioned catheter carrying a neuromodulation assembly, e.g., a neuromodulation assembly configured to use electrically-induced, thermally-induced, and/or chemically-induced approaches to modulate the renal nerves.

20 Claims, 15 Drawing Sheets

(51) Int. Cl.
  *A61B 17/32* (2006.01)
  *A61N 1/40* (2006.01)
  *A61B 18/00* (2006.01)
  *A61B 17/00* (2006.01)
(52) U.S. Cl.
  CPC .... *A61N 1/403* (2013.01); *A61B 2017/00022* (2013.01); *A61B 2017/00778* (2013.01); *A61B 2017/320069* (2017.08); *A61B 2018/0022* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00875* (2013.01); *A61B 2018/0212* (2013.01)
(58) Field of Classification Search
  CPC ........... A61B 2017/00022; A61B 2017/00778; A61B 2018/0022; A61B 2018/00267; A61B 2018/00404; A61B 2018/00434; A61B 2018/00511; A61B 2018/0577; A61B 2018/00875; A61B 2018/0212; A61N 1/403
  See application file for complete search history.

(56) References Cited

U.S. PATENT DOCUMENTS

| | | | |
|---|---|---|---|
| 8,347,891 B2 | 1/2013 | Demarais et al. | |
| 8,888,773 B2 | 11/2014 | Chang et al. | |
| 9,060,755 B2 | 6/2015 | Buckley et al. | |
| 9,084,610 B2 | 7/2015 | Goshgarian et al. | |
| 2007/0129760 A1* | 6/2007 | Demarais | A61B 18/1492 607/2 |
| 2012/0116382 A1 | 5/2012 | Ku et al. | |
| 2014/0276718 A1 | 9/2014 | Turovskiy et al. | |
| 2015/0351836 A1* | 12/2015 | Prutchi | A61B 18/1492 606/41 |
| 2016/0045257 A1* | 2/2016 | Fischell | A61M 25/00 606/33 |
| 2016/0058503 A1 | 3/2016 | Tunev et al. | |

FOREIGN PATENT DOCUMENTS

| | | |
|---|---|---|
| WO | 2015013029 A1 | 1/2015 |
| WO | 2015021835 A1 | 2/2015 |
| WO | 2015047568 A1 | 4/2015 |

OTHER PUBLICATIONS

Mark R. de Jong et al. "Renal Nerve Stimulation-Induced Blood Pressure Changes Predict Ambulatory Blood Pressure Response After Renal Denervation" Mar. 9, 2016, Hypertension 2016; 68:707-714.
Seals et al.,"Chronic sympathetic activation: consequence and cause of age-associated obesity?", American Diabetes Association, vol. 53, Feb. 2004, pp. 276-284.
FitzGerald et al., "Effects of dipping and psychological traits on morning surge in blood pressure in healthy people", Journal of Human Hypertension, Apr. 7, 2011, pp. 228-235.
Kario et al., "Research and Development of Information and Communication Technology-based Home Blood Pressure Monitoring from Morning to Nocturnal Hypertension", Elsevier Inc., vol. 82, Mar.-Apr. 2016, pp. 254-273.
Lonn et al., "Heart rate is associated with increased risk of major cardiovascular events, cardiovascular and all-cause death in patients with stable chronic cardiovascular disease: an analysis of Ontarget/ Transcend", Clin Res Cardiol, Dec. 20, 2013, pp. 149-159.
Azizi et al., "Optimum and stepped care standardised antihypertensive treatment with or without renal denervation for resistant hypertension (DENERHTN): a multicentre, open-label, randomised controlled trial", Lancet, vol. 38, May 16, 2015, pp. 1957-1965.
Townsend et al., "Catheter-based renal denervation in patients with uncontrolled hypertension in the absence of antihypertensive medications (Spyral HTN-Off Med): a randomised, sham-controlled, proof-of-concept trial", Lancet, vol. 390, Nov. 11, 2017, pp. 2160-2170.
Ukena et al., "Effects of renal sympathetic denervation on heart rate and atrioventricular conduction in patients with resistant hypertension", Int J Cardiol, Sep. 10, 2013, pp. 2846-2851.
Bohm et al., "Renal denervation reduces office and ambulatory heart rate in patients with uncontrolled hypertension: 12-month outcomes from the global Symplicity registry", Journal of Hypertension, vol. 34, Dec. 2016, pp. 2480-2486.
Dorr et al., "Beneficial effects of renal sympathetic denervation on cardiovascular inflammation and remodeling in essential hypertension", Clin Res Cardial, Oct. 18, 2014, pp. 175-184.
Zuern et al., "Effects of renal sympathetic denervation on 24-hour blood pressure variability", Front. Physiol., May 10, 2012, pp. 8.
Baroni et al., "Effects of Renal Sympathetic Denervation on Arterial Stiffness and Blood Pressure Control in Resistant Hypertensive Patients: A Single Centre Prospective Study", High Blood Press Cardiovasc Prev., vol. 22, Dec. 1, 2015, pp. 411-416.
Brandt et al., "Effects of Renal Sympathetic Denervation on Arterial Stiffness and Central Hemodynamics in Patients With Resistant Hypertension", Journal of the American College of Cardiology, vol. 60, Nov. 6, 2012, pp. 1956-1965.
Mortensen et al., "Catheter-Based Renal Sympathetic Denervation Improves Central Hemodynamics and Arterial Stiffness: A Pilot Study", The Journal of Clinical Hypertension, vol. 14, Dec. 2012, pp. 861-870.
Kario et al., Effect of Catheter-Based Renal Denervation on Morning and Nocturnal Blood Pressure:, Hypertension, vol. 66, Oct. 5, 2015, pp. 1130-1137.
Kandzari et al., "The Spyral HTN Global Clinical Trial Program: Rationale and design for studies of renal denervation in the absence (Spyral HTN Off-Med) and presence (Spyral HTN On-Med) of antihypertensive medications", American Heart Journal, vol. 171, Jan. 2016, pp. 82-91.
Esler et al., "Catheter-based renal denervation for treatment of patients with treatment-resistant hypertension: 36 month results from the Symplicity HTN-2 randomized clinical trial", European Heart Journal, vol. 35, Jun. 4, 2014, pp. 1752-1759.
Krum et al., "Percutaneous renal denervation in patients with treatment-resistant hypertension: final 3-year report of the Symplicity HTN-1 study", Lancet, vol. 383, Feb. 15, 2014, pp. 622-629.
Rosa et al., "Randomized Comparison of Renal Denervation Versus Intensified Pharmacotherapy Including Spironolactone in True-Resistant Hypertension", Hypertension, Nov. 24, 2014, pp. 407-413.
Bohm et al., "First Report of the Global Symplicity Registry on the Effect of Renal Artery Denervation in Patients With Uncontrolled Hypertension", Hypertension, Feb. 17, 2015, pp. 766-774.
"Spyral Pivotal—Spyral HTN-Off Med Study", Medtronic Vascular, accessed from https://clinicaltrials.gov/ct2/show/NCT02439749, Results first posted May 27, 2021, 11 pp.
Gorostidi, Manuel, et al., "Ambulatory blood pressure monitoring in daily clinical practice—the Spanish ABPM Registry experience", Stichting European Society for Clinical Investigation Journal Foundation, Feb. 19, 2015, 7 pages.

* cited by examiner

*Arterial Vasculature*

*Venous Vasculature*

Renal Denervation Preclinical Efficacy:
Review of 66 Treated and 64 Naïve Swine

| Group<br>N=Arteries or<br>kidneys | % Non-<br>functional<br>Area | Cortical Axon<br>Area per mm$^2$ | Mean NE<br>(pg/mg) |
|---|---|---|---|
| Naïve<br>7 day<br>N=64 | 14.6 ± 8.0 | 207.2 ± 134.6 | 264.8 ± 82.9 |
| Symplicity 7 day<br>N=54 | 56.9 ± 28.3 | 66.8 ± 84.6<br>(68% Decrease) | 92.7 ± 92.7<br>(65% Decrease) |
| Spyral 7 Day<br>N=12 | 47.3 ± 26.5 | 97.4 ± 73.1<br>(54% Decrease) | 88 ± 75<br>(68% Decrease) |

FIG. 12A

METHODS FOR TREATING PATIENTS WITH CATHETER-BASED RENAL NEUROMODULATION

CROSS-REFERENCE TO RELATED APPLICATION(S)

The present application claims priority to U.S. Provisional Patent Application No. 62/712,882, filed Jul. 31, 2018, and which is incorporated herein by reference in its entirety.

TECHNICAL FIELD

The present technology relates generally to methods and systems for treating patients with catheter-based renal neuromodulation. In particular, several embodiments are directed to treatment of patients diagnosed with hypertension and/or improving one or more measurable physiological parameters corresponding to hypertension in such patients using renal neuromodulation and associated systems and methods.

BACKGROUND

The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. As examples, radiotracer dilution has demonstrated increased renal norepinephrine (NE) spillover rates in patients with essential hypertension.

Sympathetic nerves of the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone as well as likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II calcium channel blockers), vasodilators (to counteract peripheral vasoconstriction caused by increased sympathetic drive), aldosterone blockers (to block the actions of increased aldosterone released from activation of the renin-angiotensin-aldosterone system (RAAS) and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawing(s). The components in the drawings are not necessarily to scale. Instead, emphasis is placed on illustrating clearly the principles of the present disclosure.

Panels (A) and (B) compare average morning SBP ($P_{int}$=0.090), maximum morning SBP ($P_{int}$=−0.714) and minimum morning SBP ($P_{int}$=0.041).

Figure 10:
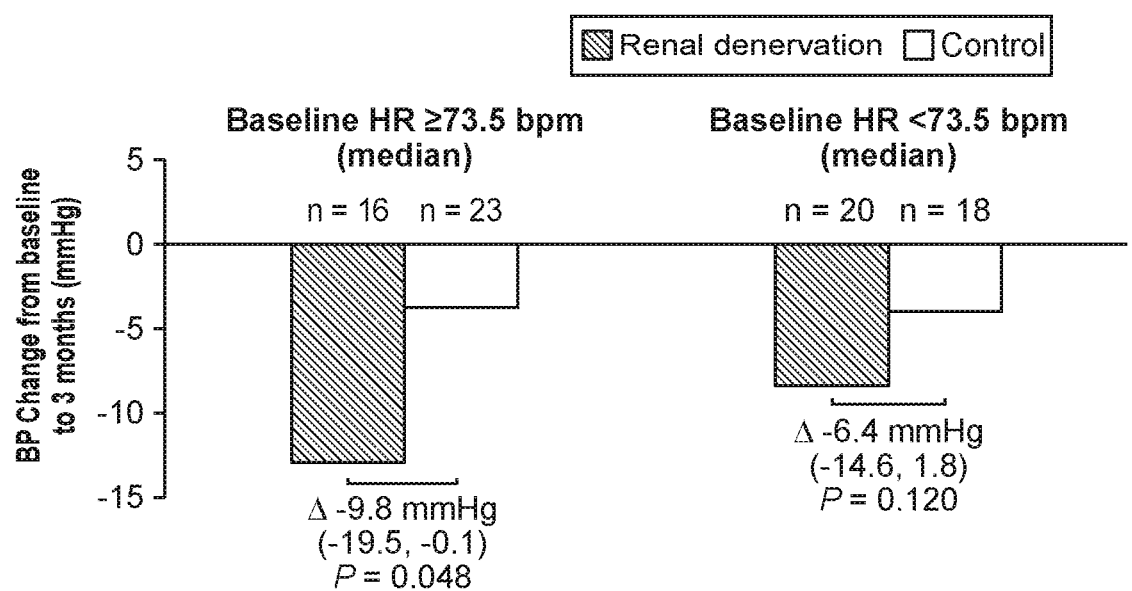

FIG. 10 shows changes in average office systolic blood pressure (SBP) in patients with a 24-hour baseline heart rate above the median (≥73.5 bpm) (left) and below the median (<73.5 bpm) (right) after renal denervation or sham procedure. Treatment differences, 95% confidence intervals and p-values were calculated from ANCOVA model, adjusting for baseline blood pressure. P-value calculated from interaction testing between baseline 24-hour heart rate and treatment effect for average office systolic blood pressure was 0.330.

Figure 11:
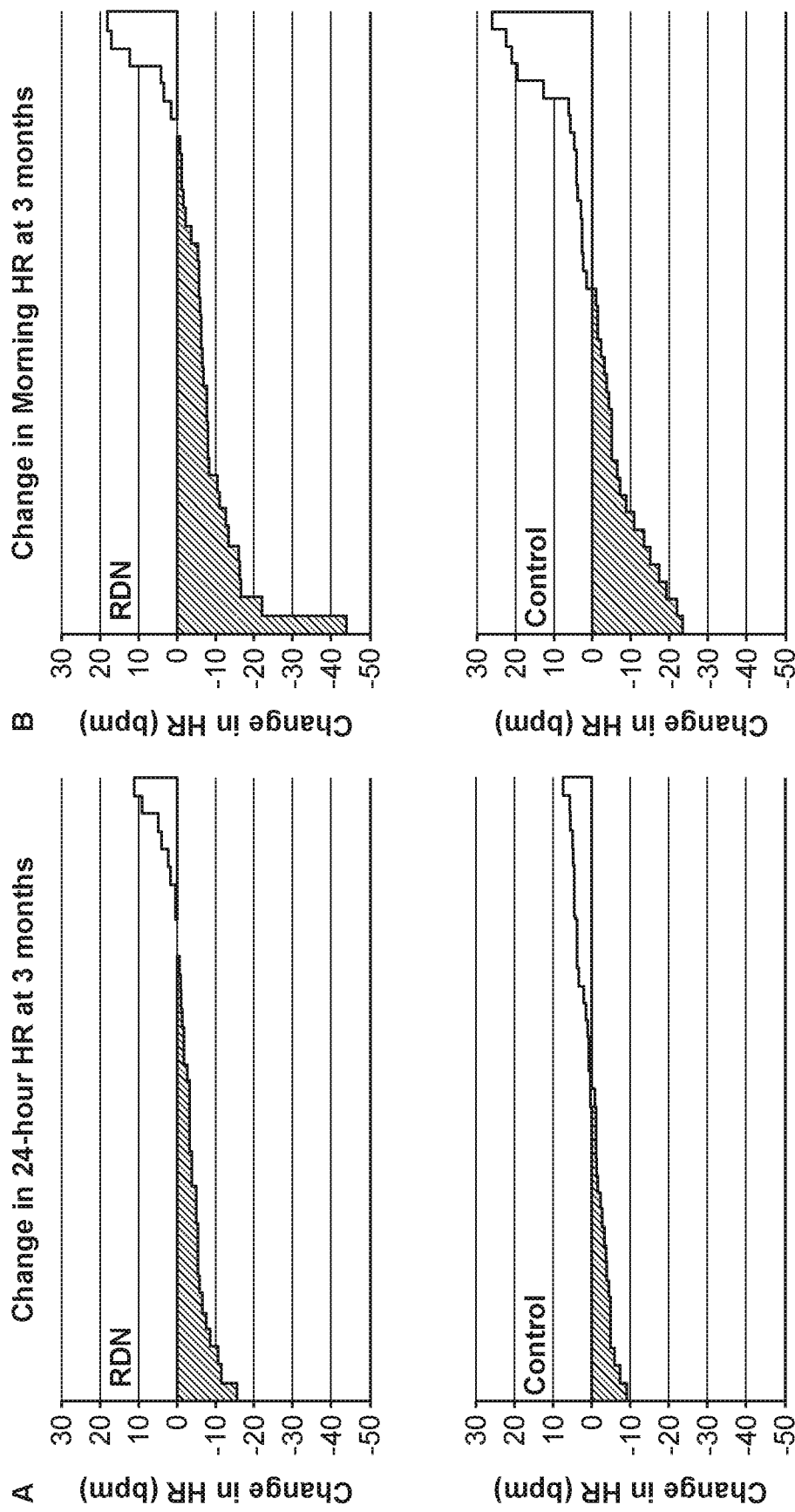
Figure 11:
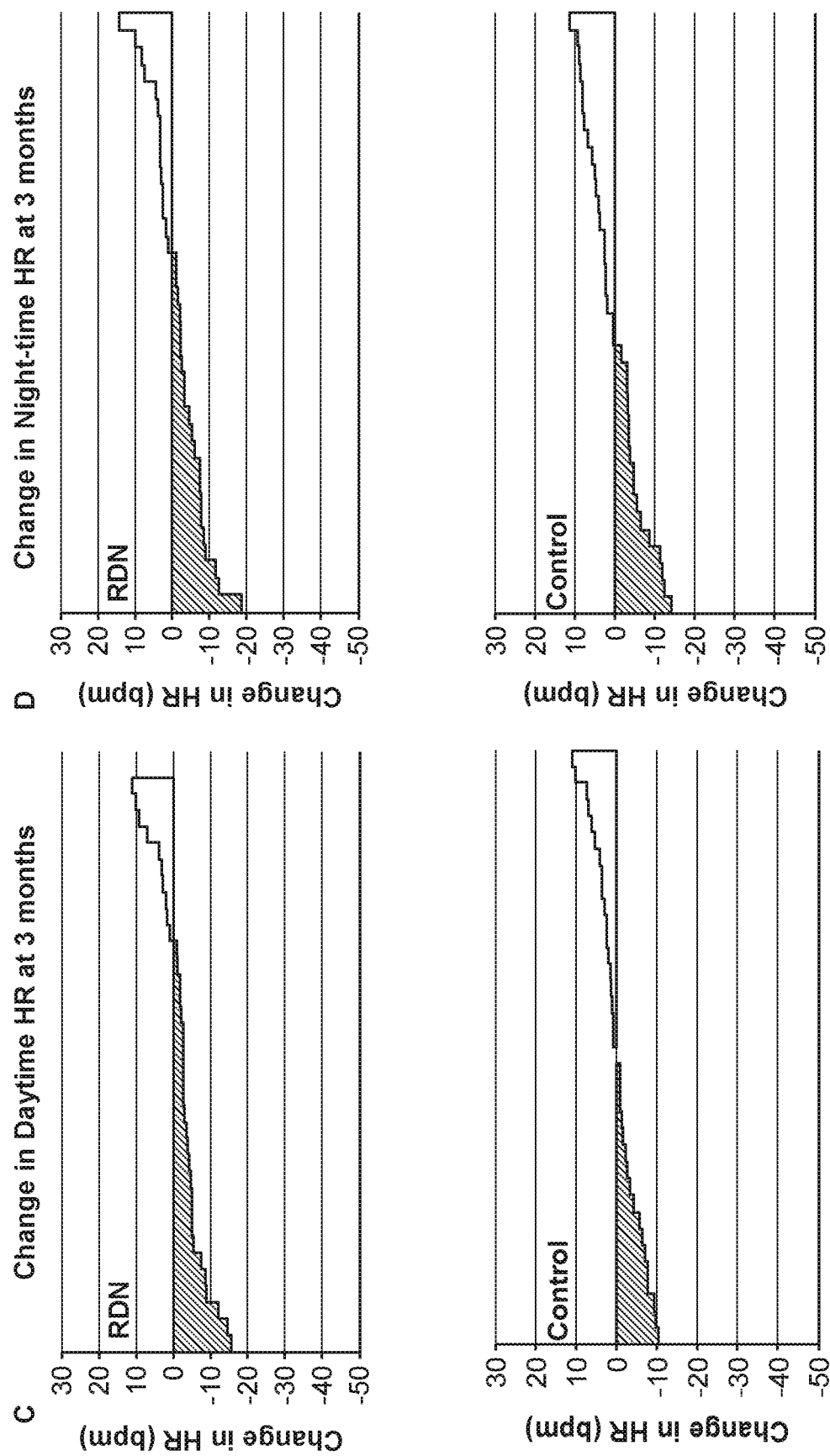

FIG. 11 shows changes at three months for individual patients in renal denervation and sham control groups for: 24-hour heart rate (HR) (Panel A); Morning HR (Panel B); Daytime HR (Panel C); and Night-time HR (Panel D) (Bpm: beats per minute; RDN: renal denervation).

FIG. 12A is a display table illustrating results from a study to determine the effects of renal denervation on cortical axon density and mean norepinephrine concentration in animal subjects.

Figure 12B:
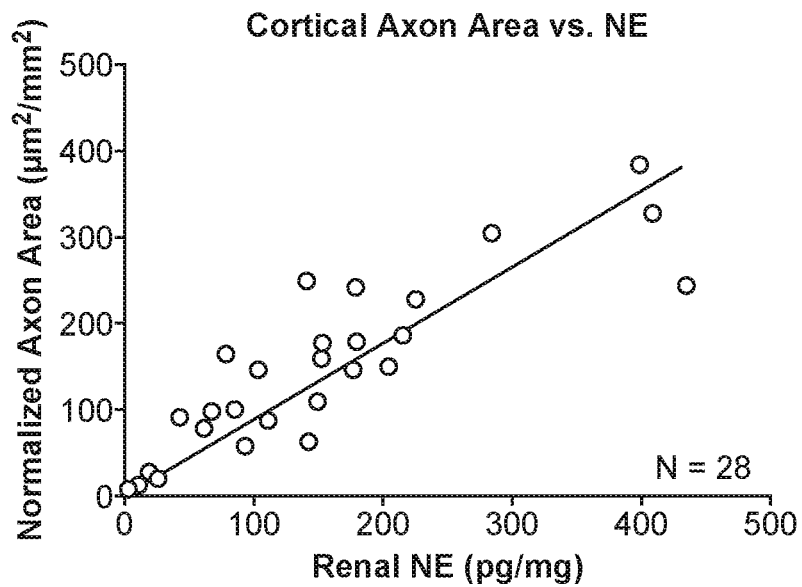
Figure 12B:
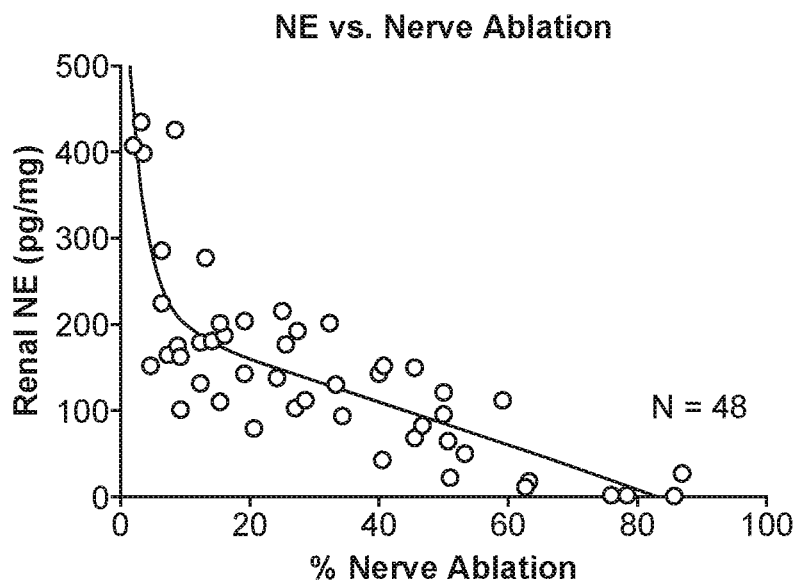

FIG. 12B is a series of graphs illustrating the response correlation between normalized cortical axon area vs. norepinephrine concentration and norepinephrine concentration vs. extent of nerve ablation along the artery of the animal subjects of FIG. 12A.

DETAILED DESCRIPTION

The present technology is directed to apparatuses, systems, and methods for treating patients diagnosed with hypertension and/or improving one or more measurable physiological parameters corresponding to hypertension in such patients using renal neuromodulation. For example, some embodiments include performing therapeutically-effective renal neuromodulation on a patient diagnosed with hypertension. In some embodiments, patients diagnosed with hypertension and exhibiting an elevated 24-hour heart rate (e.g., a heart rate at or greater than a median heart rate of a comparable population of hypertensive patients, etc.) may be treated with therapeutically-effective renal neuromodulation. Renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-12B. Although many of the embodiments are described herein with respect to electrically-induced approaches, other treatment modalities (e.g., thermally-induced, chemically-induced, etc.) in addition to those described herein are within the scope of the present technology. Additionally, several other embodiments of the technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-12B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. RENAL NEUROMODULATION FOR TREATING HYPERTENSION

A. Hypertension

High blood pressure or hypertension is characterized by an abnormal elevation of the pressure within a patient's arteries. Blood pressure is measured at an upper systolic value (e.g., about 120 mm Hg or lower for a healthy human adult) and at a lower diastolic pressure between heart beats (e.g., about 80 mm Hg or lower for a healthy human adult). In one embodiment, high blood pressure can be characterized as having prehypertension (e.g. systolic blood pressure (SBP) of about 120 mm Hg to about 139 mm Hg, diastolic blood pressure (DBP) of about 80 mm Hg to about 89 mm Hg), mild hypertension (e.g., SBP of about 140 mm Hg to about 159 mm Hg, DBP of about 90 mm Hg to about 99 mm Hg), moderate hypertension (e.g., SBP of about 160 mm Hg to about 179 mm Hg, DBP of about 100-109 mm Hg) and severe hypertension (e.g., SBP at or above 180 mm Hg, DBP at or above 110 mm Hg). In some embodiments, a person has "resistant hypertension" when that person's systolic blood pressure remains at or above 140 mm Hg despite adherence to at least three maximally tolerated doses of antihypertension medications from complementary classes, including, for example, a diuretic at an appropriate dose.

Primary or essential hypertension is a medical condition characterized by high blood pressure that can be not related to another medical condition, while secondary hypertension refers to high blood pressure that results from another medical condition relating to, for example, the kidneys, arterial health (e.g., narrowing of arteries), heart condition(s), endocrine conditions or other disorders (e.g., sleep apnea). Certain risk factors have been identified that may make an individual more likely (e.g., increase a risk) to develop hypertension during their lifetime. For example, some non-limiting, identified risk factors for increasing a likelihood of developing hypertension include having a family history of high blood pressure, age (e.g., men after 35 years of age, women after age 45), smoker, physically inactive, male gender, race, and experiencing an extended period of stress (e.g., chronic stress), among others. Moreover, age-associated stimulation of the SNS increases with adiposity and middle- and older-aged adults with progressive accumulation of body fat and/or who have lower activity (higher sedentary) levels are more likely to generate higher levels of plasma norepinephrine concentrations and spillover rates that further exacerbate vascular changes and contribute to deleterious blood pressure increases (Seals, D. R., and Bell, C., *Diabetes,* 2004, 53: 276-284).

Elevated sympathetic activity is associated with dysregulation of arterial pressure and increased sympathetic nervous system activity has been implicated as a primary precursor of hypertension. Moreover, sympathetic activation has an adverse prognostic effect in terms of development and progression of cardiovascular diseases, systemic inflammation, arterial stiffness, atherosclerosis, metabolic disorders, insulin resistance, end organ damage, risk of stroke and other cardiovascular conditions.

Additionally, with respect to blood pressure regulation, the nocturnal blood pressure of healthy individuals drops or "dips" more than 10% of the average daytime blood pressure value, which is followed by an increase in blood pressure with arousal from sleep, known as the morning surge in blood pressure (MSBP). In contrast, "elevated," i.e. limited drops in blood pressure during the night-time (e.g., night-time blood pressure reduction that is less than 10% of average daytime blood pressure) as well as excessive surge in MSBP (e.g., early morning hours), is associated with hypertension and also an increased risk of cardiovascular events and strokes even in normotensive patients (FitzGerald, L., et al., *J Hum Hypertens,* 2012, 26: 228-235; Kario, K. and Hamasaki, H., *J Clin Hypertens,* 2015, 17: 682-685). Men and older populations of patients further demonstrate "non-dipping" nocturnal blood pressure which is further associated with more sleep-related symptoms and poorer overall sleep quality as well as increased risk in cardiovascular events (Id.). Additionally, excessive MSBP and/or "non-dipping" nocturnal blood pressure may be risk factors for the development and/or the severity for hypertension, cardiovascular disease and stroke.

Heart rate is regulated by the interaction of the sympathetic and parasympathetic nervous system. High resting heart rate has been associated with cardiovascular morbidity and mortality in the general population, as well as increased incidence of hypertension, elevated risk status and worsened renal outcomes. For example, in a high-risk population where 75% had hypertension, elevated heart rate was shown to be predictive of incident heart failure (Lonn E M, et. al., *Clin Res Cardiol,* 2014; 103:149-159). Further, elevated heart rate indicates an elevated risk for heart failure hospitalization and cardiovascular death in heart failure patients.

As described further herein, aspects of the present technology are directed to the treatment of hypertensive patients, including early-stage hypertensive patients (e.g., prehypertensive patients, mild hypertensive patients, moderate hypertensive patients, severe hypertensive patients, resistant hypertensive patients, patients with a systolic blood pressure at or above 140 mm Hg, at or above 150 mm Hg, below 160 mm Hg, etc.) and having an elevated heart rate. Certain aspects of the present disclosure are directed to treating hypertensive patients having an elevated 24-hour ambulatory heart rate with renal neuromodulation. The present disclosure describes recognition that an elevated heart rate can be predictive of a beneficial and therapeutic improvement in blood pressure for such particular patients following treatment with renal neuromodulation.

B. Renal Neuromodulation

Intravascular devices that reduce sympathetic nerve activity by applying, for example, RF energy to a target site in the renal artery have been shown to reduce blood pressure in patients with hypertension. Renal denervation has revealed promising results in uncontrolled studies and in comparative, controlled studies with patients taking anti-hypertensive drugs (Azizi M, et. al., Lancet, 2015; 385:1957-1965). Additionally, renal denervation has further been shown to be effective in reducing blood pressure in hypertensive patients without medications (Townsend R R, et. al., Lancet, 2017; 390:2160-2170). Further, in patients with resistant hypertension, a reduction of heart rate after renal denervation has been observed in a single centre study (Ukena C, et. al., Int J Cardiol, 2013; 167:2846-2851) and in the large Global Symplicity Registry (Bohm M, et. al., J Hypertens, 2016; 34:2480-2486). More than 50% of patients in the latter trial received beta blockers and many other anti-hypertensive drugs, which might have confounded the effect of renal denervation on heart rate (Id.). Particular aspects of the present technology are directed to the treatment of hypertension in patients having various heart rates (e.g., heart rate above and below a median heart rate of a comparable population of hypertensive patients).

Therapeutically-effective renal neuromodulation can be used for the treatment of hypertension or for the treatment of one or more symptoms and/or sequelae associated with hypertension, the management of hypertension, or to reduce an incidence of hypertension (e.g., severe or resistant hypertension) in patients identified as having a risk of developing hypertension at a future time (e.g., having prehypertension and an elevated heart rate, having mild hypertension and an elevated heart rate, having one or more risk factors associated with the development of hypertension and an elevated heart rate).

In one embodiment, therapeutically-effective renal neuromodulation can be used to treat hypertensive patients or patients diagnosed with hypertension and having an elevated heart rate to reduce blood pressure, reduce an average daytime systolic blood pressure, reduce an average daytime diastolic blood pressure, reduce and average systolic night-time blood pressure, or reduce an average night-time diastolic blood pressure. In other embodiments, therapeutically-effective renal neuromodulation can be used to treat hypertensive patients or patients diagnosed with hypertension and having an elevated heart rate to reduce a 24-hour heart rate, reduce an average morning heart rate, reduce an average peak night-time heart rate, reduce a minimum morning heart rate or reduce a minimum moving peak morning heart rate. In another embodiment, therapeutically-effective renal neuromodulation can be used to treat hypertensive patients or patients diagnosed with hypertension and having an elevated heart rate to reduce an incidence of cardiovascular disease (e.g., coronary heart disease, etc.) or a cardiovascular event (e.g., MI, stroke, etc.) in the patient. In further embodiments, therapeutically-effective renal neuromodulation can be used for treating a patient having hypertension to improve one or more parameters associated with cardiovascular health, or to reduce a severity of a cardiovascular condition.

Figure 1:
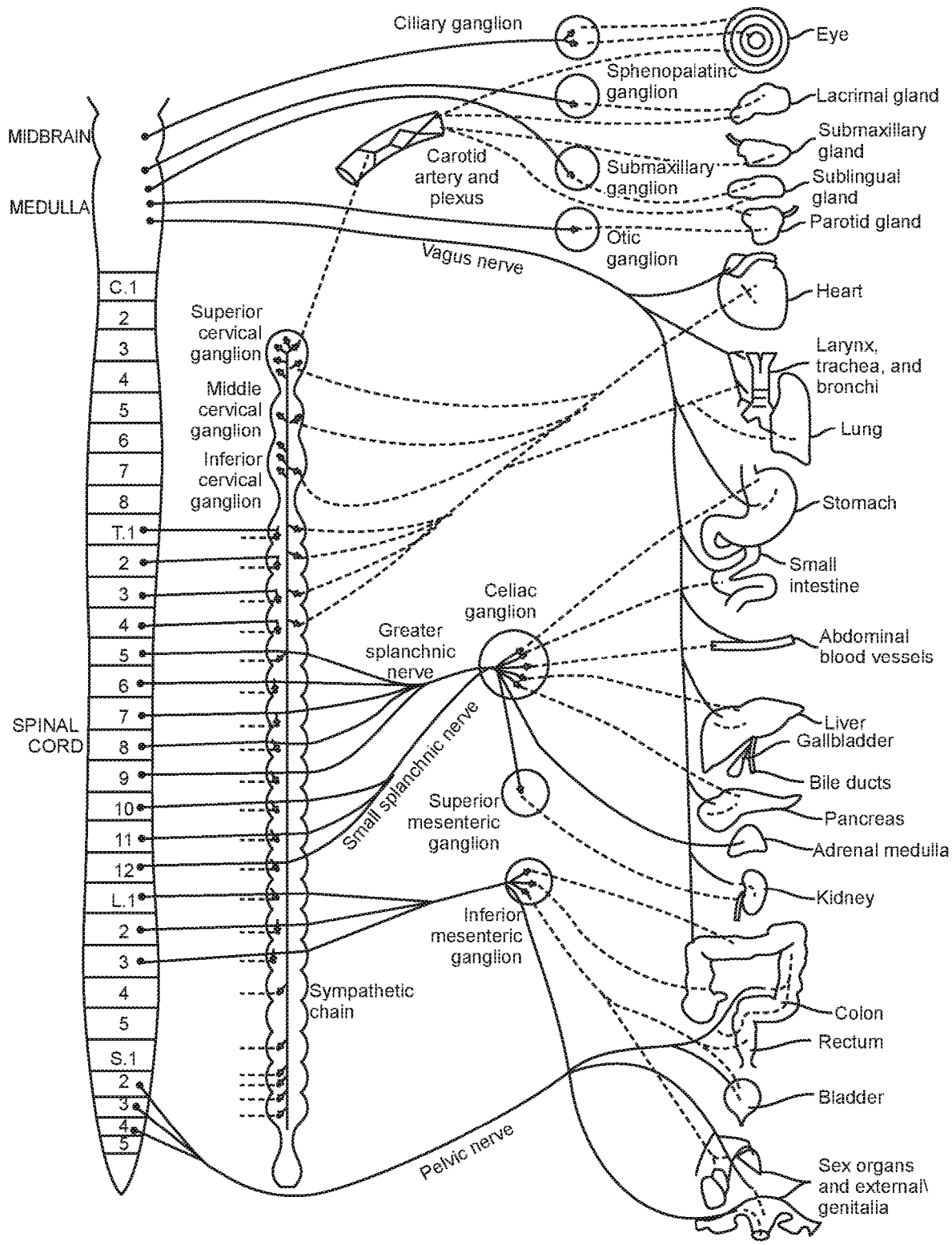
FIG. 1 is a conceptual illustration of the sympathetic nervous system (SNS) and how the brain communicates with the body via the SNS.

As shown in FIG. 1, the SNS is a branch of the autonomic nervous system along with the enteric nervous system and parasympathetic nervous system. The SNS is primarily an involuntary bodily control system typically associated with stress responses. It is always active at a basal level (called sympathetic tone) and becomes more active during times of stress. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. The SNS regulates the function of virtually all human organ systems by localized release of catecholamines (e.g., norepinephrine) from sympathetic nerve terminals innervating these tissue and organ systems, spillover of norepinephrine from vascular neuro-muscular junctions (the primary source of norepinephrine in plasma), and by systemic circulation of catecholamines (e.g., epinephrine, norepinephrine) released from the adrenal gland in response to acute, transient stress or threats. Long-term variations in basal levels, increases in basal levels due to aging, as well as spikes of circulating catecholamines from hyperactivity of the SNS responding to life circumstances can also exert more enduring regulatory effects on gene expression by altering constitutive gene expression profiles in a wide variety of tissues and organ systems.

Once released, norepinephrine binds adrenergic receptors on peripheral tissues. In addition, activation (e.g., norepinephrine release) of noradrenergic nuclei in the central nervous system (CNS) can result from transmitted impulses from activated afferent renal sympathetic neurons. Binding to adrenergic receptors either in the periphery or in the CNS causes a neuronal and hormonal response. The physiologic manifestations include pupil dilation, increased heart rate, occasional vomiting, and increased blood pressure. Increased sweating is also seen due to binding of cholinergic receptors of the sweat glands. It is known that long-term SNS hyperactivity has been identified as a major contributor to the complex pathophysiology of hypertension, states of volume overload (such as heart failure), and progressive renal disease, both experimentally and in humans. Moreover, correlative links between activation of the SNS and systemic inflammation, arterial stiffness, atherosclerosis, metabolic disorders, insulin resistance, and other cardiovascular conditions have been established.

While sympathetic drive regulation can have adaptive utility in maintaining homeostasis or in preparing many organs in the body for a rapid response to environmental factors, chronic activation of the SNS (e.g., associated with acute stress syndrome, chronic stress, primary aging, age-associated obesity, etc.) is a common maladaptive response that can contribute to diseases/conditions (e.g., hypertension, systemic or localized inflammation, vascular remodeling, atherosclerosis, obesity, insulin resistance, metabolic syndrome, etc.) or predispose individuals to physiological adaptations that can increase a patient's risk of developing resistant hypertension and/or drive progression and/or severity of hypertension in a patient. Excessive activation of the renal sympathetic nerves in particular has been identified experimentally and in humans as a likely contributor to the complex pathophysiology of hypertension, states of volume overload (such as heart failure), systemic inflammation, and progressive renal disease. As examples, radiotracer dilution has demonstrated increased renal norepinephrine spillover rates in patients with essential hypertension.

Aspects of the present technology include targeting renal nerve fibers for neuromodulation in patients (1) having been diagnosed with hypertension and demonstrating an elevated heart rate, such as a 24-hour ambulatory heart rate at or above a median heart rate for a population of hypertensive patients, and/or (2) having an increased risk associated with developing severe or resistant hypertension. For example, the patient may have mild hypertension or moderate hypertension and have a 24-hour heart rate at or above a median 24-hour heart rate for a population of hypertensive patients. In one example, the patient may have a 24-hour heart rate at or above about 73 beats per minute (BPM).

Targeting renal nerve fibers for neuromodulation in patients can effectively attenuate neural traffic along the sympathetic nerves. Without being bound by theory, attenuation of neural traffic along renal sympathetic nerves can be used, for example, to treat hypertension and/or decrease a level of severity of hypertension and/or, in another embodiment, reduce a number of anti-hypertensive medications taken by a patient.

Renal neuromodulation is the partial or complete incapacitation or other effective disruption of nerves innervating the kidneys, including nerves terminating in the kidneys or in structures closely associated with the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for alleviating symptoms and other sequelae associated with hypertension over longer periods of time, short-term modulation of the renal nerves may also be desirable. For example, some patients may benefit from short-term modulation to address acute symptoms of hypertension.

Figure 2:
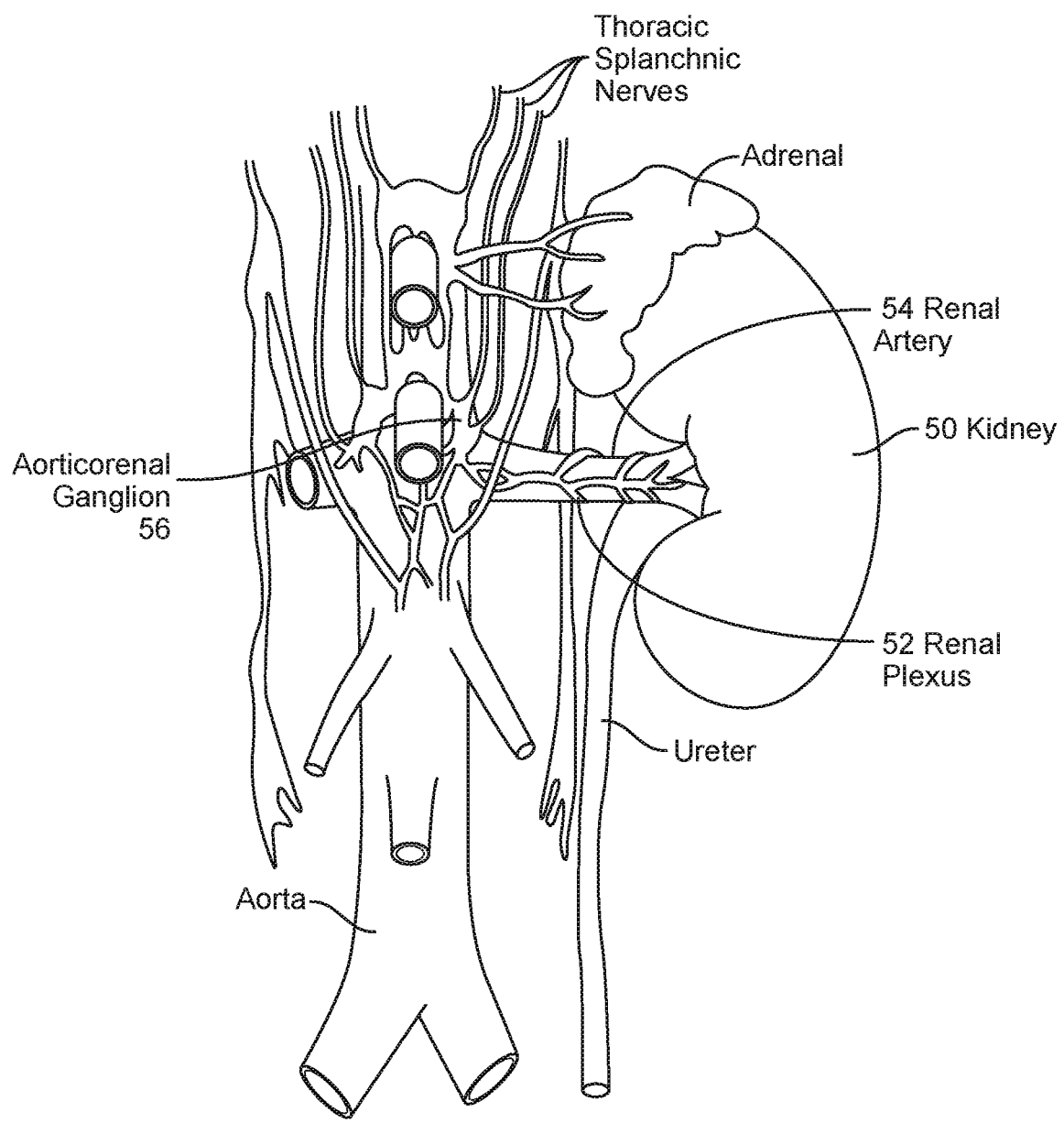
FIG. 2 is an enlarged anatomic view of nerves of a left kidney to form the renal plexus surrounding the left renal artery.

FIG. 2 is an enlarged anatomic view of nerves innervating a left kidney 50 of a patient. As FIG. 2 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidneys while terminating in the blood vessels, the juxtaglomerular apparatus, and the renal tubules (not shown). Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 1). Referring to FIGS. 1 and 2 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion (FIG. 1), the superior mesenteric ganglion (FIG. 1), and the aorticorenal ganglion 56. Postganglionic neuronal cell bodies exit the celiac ganglion, the superior mesenteric ganglion, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. Renal neuromodulation may also likely to be valuable in the treatment of diseases and conditions that are associated with hypertension and/or increased SNS tone such as, for example, cardiovascular disease, increased blood pressure variability, systemic inflammation, endothelial dysfunction, vascular inflammation, vessel remodeling and/or hardening, atherosclerosis, and metabolic disorders among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of these and other conditions associated with physiological changes that have impact on patient health. As such, renal neuromodulation is also likely to be particularly valuable in patients having one or more clinical conditions characterized by increased overall and particularly renal sympathetic activity, such as cardiovascular disease, increased blood pressure variability, low heart rate variability, systemic inflammation, chronic vascular inflammation, endothelial dysfunction, metabolic syndrome, insulin resistance, diabetes, dementia, cancer, anxiety disorder, and depression among others.

As the reduction of afferent neural signals contributes to the systemic reduction of sympathetic tone/drive, renal neuromodulation might also be useful in preventing severe or resistant hypertension. For example, a reduction in central sympathetic drive may reduce and/or improve measurable physiological parameters typically associated with the development of severe or resistant hypertension, prior to on-set of such diagnosis. Alternatively, a reduction in central sympathetic drive may, for example, reduce blood pressure, reduce an elevated heart rate, improve blood pressure variability, improve heart rate variability, increase blood flow to the brain, reduce cerebrovascular inflammation, reduce systemic inflammation, and/or improve other chronic stress-related symptoms such as generalized anxiety and sleep disturbances (e.g., insomnia, difficulty maintaining sleep, etc.). In some instances, therapeutically-effective renal neuromodulation may improve one or more measurable physiological parameters associated with a comorbid disease or condition (e.g., cardiovascular disease, stroke, high BMI (e.g., obesity), and metabolic disorder (e.g., diabetes)), in the hypertensive patient without substantially improving the blood pressure in the patient.

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in patients with hypertension as well as increased levels of peripheral inflammatory markers, such as IL-6 and CRP, in hypertensive or pre-hypertensive patients experiencing a host of inflammatory challenges.

Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to be efficacious in reducing blood pressure, decreasing blood pressure variability, decreasing nocturnal blood pressure, reducing MSBP, improving arterial stiffness and reducing mediators of systemic inflammation in patients with treatment-resistant hypertension (Dörr, O., et al., *Clin Res Cardiol*, 2015, 104: 175-184; Zuern, C. S., et al., *Front. Physiol*, 2012, 3(134): 1-8; Baroni, M., et al., *High Blood Press Cardiovasc Prev*, 2015, (4):411-6; Brandt, M. C., et al., JACC, 2012, 60(19): 1956-65; Mortensen, K., et al., *J Clin Hypertens*, 2012, 14(12): 861-870; Kario, K., et al., *Hypertension*, 2015, 66:1130-1137).

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of a renal blood vessel (e.g., renal artery, renal arterial branch, renal ostium, renal vein) and adjacent regions of the renal plexus RP, which lay intimately within or adjacent to the adventitia of the renal blood vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site.

By way of theory, targeting both general afferent and efferent renal sympathetic nerves (e.g., via a catheter-based approach, utilizing extracorporeal ultrasound) may cause beneficial effects extending well beyond affecting blood pressure, such as reducing a risk of developing hypertension, stroke, cardiovascular disease, obesity, metabolic disorder or other end organ damage. As discussed herein, a correlation between hyperactivity of the SNS, high blood pressure and elevated 24-hour ambulatory heart rate is demonstrated herein. Additionally, chronic stress, obesity and other cardiovascular maladies promote hyperactivity (e.g., overactivity) of the sympathetic nervous system throughout the body. For example, when experiencing stress, including chronic stress, hormonal and neural information (e.g., sensory afferent input) is received by the CNS, which in turn further elevates sympathetic tone via efferent signaling throughout the body. Some aspects of methods of treating patients having hypertension or having one or more risk factors (e.g., 24-hour ambulatory heart rate above a mean heart rate for a hypertensive population) using sympathetic neuromodulation are at least in part derived from the recognition described herein that the kidneys may contribute to elevated central sympathetic drive.

Several aspects of the current technology are configured to reduce renal sympathetic nerve activity within or near the kidney(s) to reduce localized release of norepinephrine. Several properties of the renal vasculature may inform the design of treatment devices and associated methods for achieving target sympathetic neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation is a useful technique in addressing hypertension. In a particular example, a pre-hypertensive patient (e.g., systolic BP of 120-139 mmHg/diastolic BP of 80-89 mmHg) may have blood pressure below the pre-hypertensive range after a renal neuromodulation procedure. Likewise, a hypertensive patient (e.g., systolic BP>140 mmHg/diastolic BP>90 mmHg) may have blood pressure below the hypertensive range after a renal neuromodulation procedure. Corresponding results may be obtained with angiotensin II levels, plasma aldosterone concentration, plasma renin activity, and/or aldosterone-to-renin ratio. For example, a reduction in an aldosterone-to-renin ratio can be, for example, by at least about 5%, 10% or a greater amount (e.g., about 50%, about 80%, about 90%) as determined by blood analysis and calculation before and after (e.g., 1, 3, 6, or 12 months after) a renal neuromodulation procedure.

Renal neuromodulation may prevent or reduce an incidence of developing one or more comorbid conditions or diseases in a patient with hypertension. For example a patient with prehypertension or hypertension treated with renal neuromodulation may have a decreased likelihood of developing cardiovascular disease, stroke risk, metabolic disorders, insulin resistance, diabetes, systemic inflammation, etc. In another embodiment, patients with hypertension having one or more comorbid conditions or diseases may have an improvement in (e.g., reduction, maintain a level, slow a rate of progression of) in the one or more comorbid conditions or diseases and associated symptoms thereof.

Treatment of hypertension may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

II. METHODS FOR TREATING HYPERTENSION

Disclosed herein are several embodiments of methods directed to treating hypertension in a patient using catheter-based renal neuromodulation. In other embodiments, methods are directed to treatment of other conditions related to hypertension and/or comorbid with hypertension via renal neuromodulation. The methods disclosed herein may represent various advantages over a number of conventional approaches and techniques in that they allow for the potential targeting of causes(s) of hypertension and/or improving one or more measurable physiological parameters corresponding to hypertension. In certain embodiment, the methods disclosed herein allow for the identification and treatment of a subpopulation of hypertensive patients that can achieve a greater decrease in blood pressure than a comparable population of hypertensive patients following neuromodulation treatment. Elevated sympathetic drive, which may either be a cause of several neurological, immune vascular, or other physiological risk factors associated with hypertension or a key mediator of hypertension manifestation can be reduced via renal neuromodulation in afflicted/identified patients. Also, the disclosed methods provide for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity. For example, renal neuromodulation is expected to reduce a level of central sympathetic activity that may contribute to one more underlying causes of hypertension. In some embodiments, renal neuromodulation is expected to reduce a blood pressure level in the identified and treated patient.

In one embodiment, a hypertensive patient having a 24-hour heart rate at or above a median heart rate for a population of hypertensive patients can be treated with neuromodulation. In certain embodiments of the methods provided herein, renal neuromodulation is expected to result in a change in blood pressure, heart rate (e.g., 24-hour heart rate), sympathetic nerve activity and/or in other measurable physiological parameters or markers, over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring blood pressure, heart rate, and/or sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure (e.g., immediately, after a predetermined period of time, repeated procedures at set periods of time, or in other cases for a specific patient population such as patients that have experienced a sufficient drop in blood pressure by 3 months, etc.). In certain embodiments, a baseline blood pressure, heart rate and/or sympathetic nerve activity level is derived from the subject undergoing treatment. For example, baseline blood pressure, heart rate and/or sympathetic nerve activity level may be measured in the subject at one or more timepoints prior to treatment. A baseline blood pressure, heart rate and/or sympathetic nerve activity value may represent sympathetic nerve activity at a specific timepoint before neuromodulation, or it may represent an average activity level at two or more timepoints prior to neuromodulation. In certain embodiments, the baseline value is based on blood pressure, heart rate and/or sympathetic nerve activity immediately prior to treatment (e.g., after the subject has already been catheterized). Alternatively, a baseline value may be derived from a standard value for blood pressure, heart rate and/or sympathetic nerve activity observed across the population as a whole or across a particular subpopulation. In other embodiments, a baseline value may be derived from a blood pressure, heart rate and/or sympathetic nerve activity observed in a comparable patient having a 24-hour heart rate below a median heart rate for a population of hypertensive patients. In certain embodiments, post-neuromodulation blood pressure, heart rate and/or sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease blood pressure, heart rate and/or sympathetic nerve activity to a target level. In these embodiments, the methods include a step of measuring blood pressure, heart rate and/or sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target blood pressure, heart rate and/or sympathetic nerve activity level is reached. In other embodiments, the methods are simply designed to decrease blood pressure, heart rate and/or sympathetic nerve activity below a baseline level without requiring a particular target activity level.

In one embodiment, measured norepinephrine content (e.g., assessed via tissue biopsy, assessed in real-time via intravascular blood collection techniques, assessed in real-time via urine, etc.) can be reduced (e.g., at least about 5%, 10%, 20% or by at least 40%) in the patient within, for example, about three months after at least partially inhibiting sympathetic neural activity in nerves proximate a renal blood vessel.

In one embodiment, renal neuromodulation may be performed on a hypertensive patient having a baseline 24-hour heart rate at or greater than a median heart rate of a population of hypertensive patients to reduce one or more measurable physiological parameters corresponding to the hypertension. In various embodiments, the hypertensive patient has a baseline systolic blood pressure of at least approximately 150 mm Hg. In other embodiments, the hypertensive patient has a baseline systolic blood pressure of less than approximately 180 mm Hg, less than approximately 175 mm Hg, less than approximately 170 mm Hg, less than approximately 165 mm Hg, less than approximately 160 mm Hg, less than approximately 155 mm Hg, less than approximately 150 mm Hg, less than approximately 145 mm Hg, at least about 140 mm Hg, between about 140 mm Hg to about 159 mm Hg, between about 160 mm Hg and about 179 mm Hg. In a further embodiment, the patient is prehypertensive (e.g., systolic blood pressure of between about 120 mm Hg and about 139 mm Hg). In further embodiments, the hypertensive patient has mild hypertension and a baseline systolic blood pressure of between approximately 150 mm Hg and 159 mm Hg. In some embodiments, the 24-hour median heart rate of a population of hypertensive patients is about 70 beats per minute (bpm), 71 bpm, 71.5 bpm, 72 bpm, 72.5 bpm, 73 bpm, 73.5 bpm, 74 bpm, 74.5 bpm, about 75 bpm, about 75.5 bpm, about 76 bpm, over 76 bpm, or under 70 bpm. For example, a 24-hour median heart rate of a population of hypertensive patients is about 73 bpm or about 73.5 bpm.

In some embodiments, for example, a hypertensive patient having a 24-hour heart rate at or above a median heart rate for a population of hypertensive patients that undergoes renal neuromodulation may result in a reduction in blood pressure (e.g., systolic blood pressure, diastolic blood pressure) greater than a comparable patient having a 24-hour heart rate below the median heart rate. In one embodiment, such a hypertensive patient may, for example, have an office systolic blood pressure of at least approximately 150 mm Hg and/or an office diastolic blood pressure of at least approximately 90 mm Hg. In another embodiment, the patient may have a mean 24-hour ambulatory systolic blood pressure (ASBP) of between at least about 140 mm Hg and about 170 mm Hg. In a further embodiment, the patient may be prehypertensive or have mild hypertension. In certain embodiments, neither the patient and/or the comparable patient is taking anti-hypertensive medication (e.g., beta blockers, etc.). In various embodiments, a reduction in systolic blood pressure, diastolic blood pressure, and/or 24-hour ambulatory systolic blood pressure by about 1%, 1.5%, 2%, 2.5%, 3%, 3.5%, 4%, 5%, 6%, 7%, 8%, 9%, 10%, 12%, 15% or a greater amount can be achieved following renal neuromodulation.

In some embodiments, a hypertensive patient having the 24-hour heart rate at or above the median heart rate may achieve a decrease in average 24-hour systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg or greater amount more than a comparable patient having a 24-hour heart rate below the median heart rate. In some embodiments, a hypertensive patient having the 24-hour heart rate at or above the median heart rate may achieve a decrease in average 24-hour diastolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg or greater amount more than a comparable patient having a 24-hour heart rate below the median heart rate.

In some embodiments, a hypertensive patient having the 24-hour heart rate at or above the median heart rate may achieve at one of a greater reduction in average morning heart rate, a greater reduction in average peak night-time heart rate, a greater reduction in minimum morning heart rate, and a greater reduction in minimum moving peak morning heart rate, than the comparable patient having a 24-hour heart rate below the median heart rate following treatment. For example, a reduction in 24-hour rate, average morning heart rate, average peak night-time heart rate, minimum morning heart rate and/or minimum moving peak morning heat rate by about 1%, 1.5%, 2%, 2.5%, 3%, 3.5%, 4%, 5%, 6%, 7%, 8%, 9%, 10%, or a greater amount can be achieved following renal neuromodulation.

In one embodiment, a hypertensive patient having the 24-hour heart rate at or above the median heart rate may achieve greater reduction in at least one of peak morning heart rate and average morning heart rate surge than the comparable patient having a 24-hour heart rate below the median heart rate following treatment.

In another embodiment, a hypertensive patient having the 24-hour heart rate at or above the median heart rate may achieve greater reduction in average morning systolic blood pressure than the comparable patient having a 24-hour heart rate below the median heart rate following treatment. In other embodiments, a hypertensive patient having the 24-hour heart rate at or above the median heart rate may achieve greater reduction in one or more of average daytime systolic blood pressure, average daytime diastolic blood pressure, average night-time systolic blood pressure, and average night-time diastolic blood pressure than the comparable patient having a 24-hour heart rate below the median heart rate following treatment. For example, a reduction in average daytime systolic blood pressure, average daytime diastolic blood pressure, average night-time systolic blood pressure, and/or average night-time diastolic blood pressure by about 1%, 1.5%, 2%, 2.5%, 3%, 3.5%, 4%, 5%, 6%, 7%, 8%, 9%, 10%, or a greater amount can be achieved following renal neuromodulation. In some embodiments the reduction in blood pressure is achieved within 3, 6, 12 or more months following treatment.

In some embodiments, a hypertensive patient having the 24-hour heart rate at or above the median heart rate may achieve a decrease in average daytime systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg or greater amount more than a comparable patient having a 24-hour heart rate below the median heart rate. In some embodiments, a hypertensive patient having the 24-hour heart rate at or above the median heart rate may achieve a decrease in average daytime diastolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg or greater amount more than a comparable patient having a 24-hour heart rate below the median heart rate. In other embodiments, a hypertensive patient having the 24-hour heart rate at or above the median heart rate may achieve a decrease in average night-time systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg or greater amount more than a comparable patient having a 24-hour heart rate below the median heart rate. In still other embodiments, a hypertensive patient having the 24-hour heart rate at or above the median heart rate may achieve a decrease in average night-time diastolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg or greater amount more than a comparable patient having a 24-hour heart rate below the median heart rate.

In further embodiments, a hypertensive patient having the 24-hour heart rate at or above the median heart rate may achieve a decrease in average morning systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg or greater amount more than a comparable patient having a 24-hour heart rate below the median heart rate. In yet further embodiments, a hypertensive patient having the 24-hour heart rate at or above the median heart rate may achieve a decrease in maximum morning systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg, or greater amount more than a comparable patient having a 24-hour heart rate below the median heart rate. In still further embodiments, a hypertensive patient having the 24-hour heart rate at or above the median heart rate may achieve a decrease in minimum morning systolic blood pressure of at least approximately 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg, or greater amount more than a comparable patient having a 24-hour heart rate below the median heart rate.

In an example, a method for treating hypertension can include selecting a patient having a baseline systolic blood pressure of at least about 140 mm Hg, at least about 145 mm Hg, or at least about 150 mm Hg, and a baseline 24-hour heart rate of at least approximately 70 bmp, 71 bpm, 72 bpm, 73 bpm, 74 bpm or 75 bpm, and intravascularly delivery an energy delivery element to a renal artery of the selected patient. The method can further include modulating a renal nerve along the renal artery by delivering energy from the energy delivery element positioned along a wall of the renal artery, wherein the selected patient achieves a greater decrease in blood pressure following treatment than a patient having a baseline systolic blood pressure of at least 140 mm Hg, at least 145 mm Hg, or at least 150 mm Hg, and a baseline 24-hour heart rate less than the selected patient, and following a comparable treatment.

In some embodiments, following treatment, the selected patient may further achieve one or more of a greater reduction in average morning heart rate, a greater reduction in average peak night-time heart rate, a greater reduction in minimum morning heart rate, and a greater reduction in minimum moving peak morning heart rate, then the patient with the baseline 24-hour heart rate less than the selected patient, and following a comparable treatment. In further embodiments, following treatment the selected patient may further achieve a greater reduction in at least one of peak morning heart rate and average morning heart rate surge then the patient with the baseline 24-hour heart rate less than the selected patient, and following a comparable treatment.

In other embodiments, following treatment, the selected patient may further achieve a greater reduction in average morning systolic blood pressure, maximum morning systolic blood pressure and/or minimum morning systolic blood pressure than the patient with the baseline 24 heart rate less than the selected patient, and following a comparable treatment. In still further embodiments, following treatment, the selected patient may achieve a greater reduction in average daytime systolic blood pressure, average daytime diastolic blood pressure, average night-time systolic blood pressure and/or average night-time diastolic blood pressure than the patient with the baseline 24-hour heart rate less than the selected patient, and following a comparable treatment.

In one embodiment, a decrease in sympathetic nerve activity may be observed via a marker of sympathetic nerve activity in selected patients, such as decreased levels of plasma norepinephrine (noradrenaline), changes in levels of systemic renin in plasma, changes in levels of angiotensin II in plasma, and/or changes in levels of systemic aldosterone in plasma. Other known measures or markers of sympathetic nerve activity can include MSNA, norepinephrine spillover, and/or heart rate variability.

In some instances, a decrease in SNS activity can be observed as a decrease in norepinephrine and metabolites thereof (e.g., vanillomandelic acid (VMA)) in urine. In another embodiment, other measurable physiological parameters or markers, such as improved baroreceptor sensitivity, improved heart rate responses to stimuli/stress, improved heart rate variability, improved skin conductance, improved blood pressure variability (e.g., improved MSBP, improved nocturnal blood pressure "dipping"), lower levels of peripheral inflammatory biomarkers (e.g., IL-6, IL-1β, IL-2, TNF-α, CRP, etc.), improved levels of NPY, reduced cortisol levels, reduced CAR, reduced glucocorticoid resistance, improved brain neural activity (e.g., in the hippocampus and other brain regions), cessation or reversal of brain atrophy (e.g., in the hippocampus), changes in aldosterone-to-renin ratio (ARR), changes in a salt suppression test, changes in blood plasma levels of potassium, improved blood glucose regulation, etc., can be used to assess efficacy of the thermal modulation treatment for patients diagnosed with hypertension. In certain embodiments, renal neuromodulation may be repeated one or more times at various intervals until a desired sympathetic nerve activity level or another therapeutic benchmark is reached for selected hypertensive patients.

Renal neuromodulation may be performed on a patient with hypertension and a heart rate (e.g., a 24-hour heart rate) at or above a median heart rate for a population of hypertensive patients. In some embodiments, for example, renal neuromodulation may result in a reduction in a patient's heart rate under stress, may raise heart rate variability, lower a MSBP, lower a nocturnal blood pressure level, reduce systolic blood pressure, reduce blood pressure variability, increase baroreceptor sensitivity, lower skin conductance, reduce a serum level of an inflammatory biomarker, or reduce a level of insulin resistance. In a particular example, a patient having hypertension and decreased heart rate variability (e.g., SDNN<50 ms) may have heart rate variability within a normal range (e.g., SDNN>50 ms) after a neuromodulation procedure. In a further example, a reduction in MSBP can be, for example, by at least about 5%, 10% or a greater amount as determined by average ambulatory blood pressure analysis before and after (e.g., 1, 3, 6, or 12 months after) a renal neuromodulation procedure. Likewise, and in yet a further example, a reduction in nocturnal blood pressure level can be, for example, by at least about 5%, 10%, or a greater amount as determined by average ambulatory blood pressure analysis before and after (e.g., 1, 3, 6, or 12 months after) a renal neuromodulation procedure.

Renal neuromodulation may be performed on a patient diagnosed with hypertension to reduce one or more measurable physiological parameters corresponding to the hypertension. In some embodiments, renal neuromodulation may decrease blood pressure, decrease aldosterone-to-renin ratio, change the result of a salt suppression test (e.g., negative result), increase blood plasma levels of potassium, etc. For example, renal neuromodulation may reduce the severity and/or frequency of hypertension in a selected patient. A reduction in blood pressure can be, for example, by at least about 5%, 10%, or a greater amount as determined by average blood pressure analysis before and after (e.g., 1, 3, 6, or 12 months after) a renal neuromodulation procedure. Corresponding results may be obtained with plasma aldosterone concentration, plasma renin activity, aldosterone-to-renin ratio, and/or blood plasma levels of potassium (e.g., to assess reversal of a hypokalemia state). A reduction in plasma aldosterone concentration can be, for example, by at least about 5%, 10% or a greater amount as determined by blood analysis. In a specific example, plasma aldosterone concentration can be reduced by an amount up to about 90% as determined by blood analysis. In another instance, a reduction in an aldosterone-to-renin ratio can be, for example, by at least about 5%, 10% or a greater amount (e.g., about 50%, about 80%, about 90%) as determined by blood analysis and calculation.

In the case of secondary hypertension, renal neuromodulation may provide a reduction in plasma renin activity, for example, by about 5%, 10% or a greater amount as determined by blood analysis. In a specific example, plasma renin activity can, for example, be reduced by an amount up to about 80% as determined by blood analysis. Additionally, an increase in blood plasma levels of potassium can be, for example, by about 5%, 10% or a greater amount as determined by blood analysis. For example, normal plasma potassium levels are approximately between 3.5 to about 5.0 mEq/L. Accordingly, hypokalemia can be characterized by a plasma potassium level less than about 3.5 mEq/L.

In addition to or instead of affecting the blood pressure or hypokalemia in a selected patient, renal neuromodulation may efficaciously treat other measurable physiological parameter(s) or sequelae corresponding to hypertension. For example, in some embodiments, renal neuromodulation may reduce the severity and/or frequency of headaches, muscle cramps/spasms, muscle fatigue, numbness, tingling, metabolic alkalosis, polyuria, polydipsia, and/or patient reported fatigue. Furthermore, renal neuromodulation may improve markers of renal injury (e.g., serum BUN levels, serum creatinine levels, serum cystatin C levels, proteinuria levels, NGAL levels, and Kim-1 levels) or may improve renal function (e.g., slow a decline in glomerular filtration rate) in a patient, prevent end-stage renal disease, etc. These and other results may occur at various times, e.g., directly following renal neuromodulation or within about 1 month, 3 months, 6 months, a year, or a longer period following renal neuromodulation.

As previously discussed, the progression of hypertension may be related to sympathetic overactivity and, correspondingly, the degree of sympathoexcitation in a patient may be related to the severity of the clinical presentation of the hypertension. The kidneys are strategically positioned to be both a cause (via afferent nerve fibers) and a target (via efferent sympathetic nerves) of elevated central sympathetic drive. In some embodiments, renal neuromodulation is used to reduce central sympathetic drive in a patient diagnosed with hypertension in a manner that treats the patient for the hypertension and/or sequelae associated with hypertension. In some embodiments, for example, MSNA can be reduced by at least about 10% in the patient within about three months after at least partially inhibiting sympathetic neural activity in nerves proximate a renal artery of the kidney. Similarly, in some instances whole body NE spillover can be reduced at least about 20% in the patient within about three months after at least partially inhibiting sympathetic neural activity in nerves proximate a renal artery of the kidney. Additionally, measured NE content (e.g., assessed via renal biopsy, assessed in real-time via intravascular blood collection techniques, etc.) can be reduced (e.g., at least about 5%, 10%, or by at least 20%) in the patient within about three months after at least partially inhibiting sympathetic neural activity in nerves proximate a renal artery innervating the kidney.

In one example, a patient diagnosed with hypertension and having an elevated heart rate can be subjected to a baseline assessment indicating a first set of measurable parameters corresponding to the hypertension. Such parameters can include, for example, blood pressure, heart rate, sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, levels of central sympathetic drive (e.g., MSNA, whole body NE spillover), and markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment), the patient can be subjected to a follow-up assessment. The follow-up assessment can indicate a measurable improvement in one or more physiological parameters corresponding to the hypertension.

The methods described herein address the sympathetic excess that is thought to be an underlying cause of hypertension or a central mechanism through which hypertension manifests its multiple deleterious effects on patients. In contrast, pharmaceutical therapies currently prescribed for patients having hypertension typically address only specific manifestations of hypertension. Additionally, these known therapies can have significant limitations including limited efficacy, undesirable side effects and can be subject to adverse or undesirable drug interactions when used in combination. Moreover, conventional therapies may require the patient to remain compliant with the treatment regimen over time. In contrast, renal neuromodulation can be a one-time or otherwise limited treatment that would be expected to have durable benefits to inhibit the long-term disease progression and thereby achieve a favorable patient outcome.

In some embodiments, patients diagnosed with hypertension can be treated with renal neuromodulation alone. However, in other embodiments, patients diagnosed with hypertension can be treated with one or more combinations of therapies for treating primary causative modes of hypertension and/or sequelae of hypertension. For example, combinations of therapies can be tailored based on specific manifestations of the disease in a particular patient. In a specific example, patients having hypertension and presenting hypertension can be treated with both antihypertensive drugs and renal neuromodulation and/or other forms of tissue modulation (e.g., carotid body modulation, etc.). In another example, renal neuromodulation can be combined with angiotensin-converting-enzyme (ACE) inhibitors (e.g., Captopril, Zofenopril, Enalapril, Ramipril, Fosinopril, etc.) or angiotensin receptor blockers (ARBs) (e.g., Valsartan, Telmisartan, Losartan, etc.) to treat secondary hypertension.

Primary hypertension can be treated using a combination of renal neuromodulation and surgical removal of a focal aldosterone producing adenoma (e.g., adrenalectomy) or drugs that block the secretion of aldosterone (e.g., spironolactone, eplerenone). In patients also experiencing hypokalemia, intravenous (IV) supplementation, oral potassium chloride supplements, and/or dietary modifications can accompany renal neuromodulation.

In the case of systemic inflammation and/or a patient having elevated serum levels of inflammatory biomarkers, IL-6, IL-1β, IL-2, TNF-α and/or CRP, renal neuromodulation may improve (e.g., reduce a level of) markers of inflammation (e.g., IL-6, IL-1β, 11-2, TNF-α, CRP), and in some embodiments, provide a reduction in biomarker level, for example, by about 5%, 10%, 25%, 45% or a greater amount as determined by blood analysis before and after (e.g., 1, 3, 6, or 12 months after) a renal neuromodulation procedure. In an example where the patient has elevated cortisol levels, elevated CRH levels, and/or glucocorticoid resistance, renal neuromodulation may improve (e.g., reduce a level of) cortisol levels, CRH levels, and/or glucocorticoid resistance by about 5%, about 10%, about 20% or greater amount as determined by quantitative analysis (e.g., dexamethasone binding assay, dexamethasone suppression test, radioimmunoassay, CRH stimulation test, etc.). In other embodiments, and in particular afflicted patients, renal neuromodulation may increase arteriole blood flow, reduce a level of atherosclerosis, or reduce a degree of arterial stiffening in the patient by about 5%, 10% or a greater amount as determined by qualitative or quantitative analysis (e.g., computerized tomography (CT) scan, pulse wave velocity (PWV) analysis, angiography, etc.) before and after (e.g., 1, 3, 6, or 12 months after) a renal neuromodulation procedure.

In another embodiment, renal neuromodulation may be performed on a prehypertensive patient having a 24-hour ambulatory heart rate above a median heart rate for a population of hypertensive patients. Renal neuromodulation is expected to therapeutically improve the patient's risk of developing hypertension, including resistant hypertension.

III. SELECTED EXAMPLES OF NEUROMODULATION MODALITIES

As noted previously, complete or partial neuromodulation of a target renal sympathetic nerve in accordance with embodiments of the present technology can be electrically-induced, thermally-induced, chemically-induced, or induced in another suitable manner or combination of manners at one or more suitable locations along one or more renal blood vessels during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, radiation (e.g., infrared, visible, gamma), or cryotherapeutic energy, chemicals (e.g., drugs or other agents), or combinations thereof. Where a system uses a monopolar configuration, a return electrode or ground patch fixed externally on the subject can be used. In certain embodiments, neuromodulation may utilize one or more devices including, for example, catheter devices such as the Symplicity™ catheter (Medtronic, Inc.). Other suitable thermal devices are described in U.S. Pat. Nos. 7,653,438, 8,347,891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. Other examples of suitable direct heat devices are described in International Patent Application No. PCT/US2014/023738 filed Mar. 11, 2014, and U.S. patent application Ser. No. 14/203,933, filed Mar. 11, 2014. All of the foregoing patent references are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities. In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a renal sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion.

Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys to pulse. Cryogenic adhesion also can facilitate intravascular or intraluminal positioning, particularly in relatively small structures (e.g., renal branch arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, monitoring, assessing and/or determining neuromodulation efficacy can be accomplished by detecting changes in the level of one or more surrogate biomarkers (e.g., a biomarker that directly or indirectly correlates with sympathetic nerve activity in the patient, a biomarker that directly or indirectly correlates with hypertension, arterial stiffness and/or an inflammatory response in the patient) in serum, plasma and/or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

IV. SELECTED EMBODIMENTS OF RENAL NEUROMODULATION SYSTEMS AND DEVICES

Figure 3:
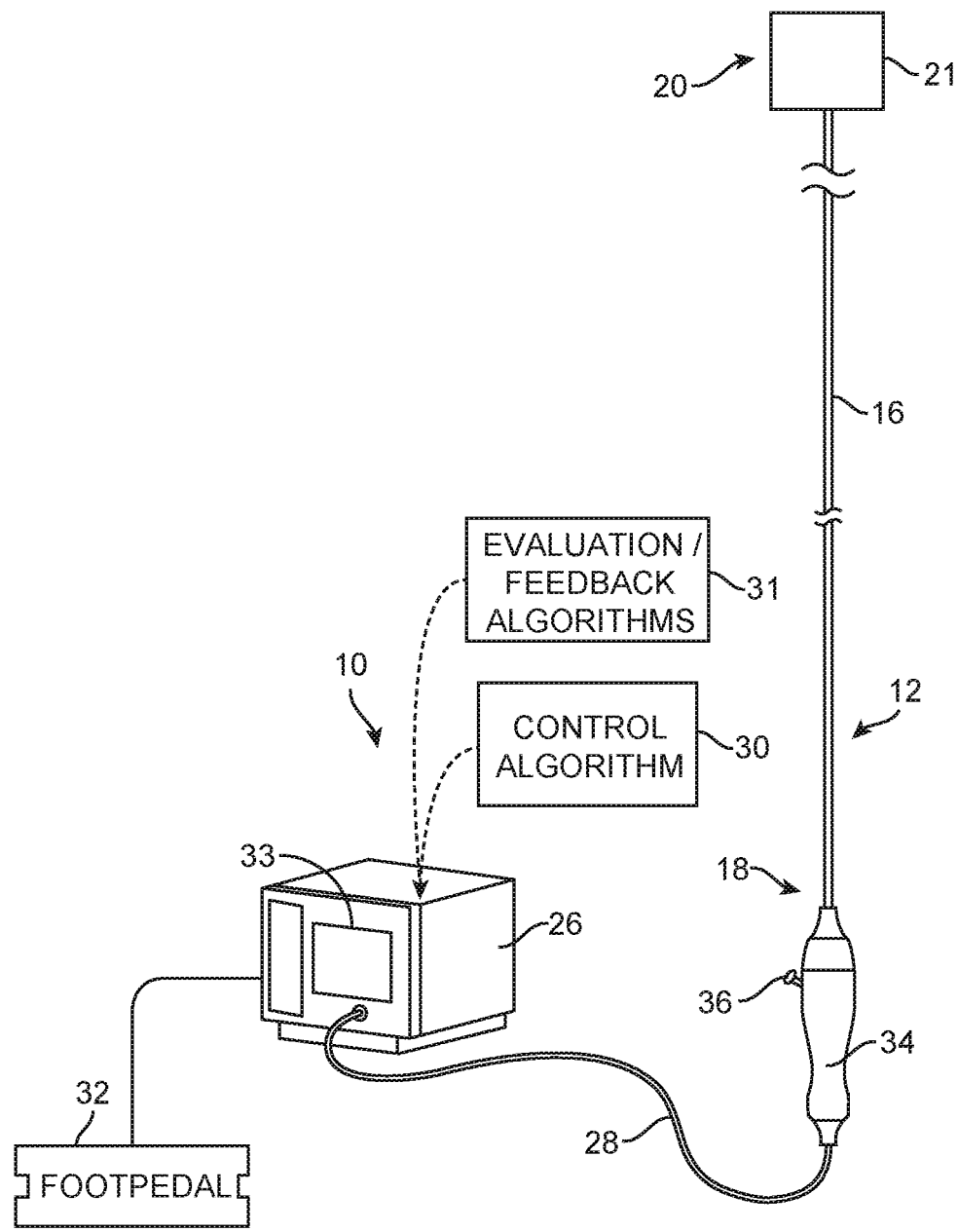
FIG. 3 illustrates an intravascular neuromodulation system configured in accordance with an embodiment of the present technology.

FIG. 3 illustrates a renal neuromodulation system 10 configured in accordance with an embodiment of the present technology. The system 10, for example, may be used to perform therapeutically-effective renal neuromodulation on a patient (a) to reduce a blood pressure, (b) to reduce a 24-hour heart rate, (c) to reduce a severity of symptoms relating to hypertension, and/or (d) to treat and/or prevent development of one or more comorbid conditions/diseases associated with hypertension (e.g., cardiovascular disease, stroke risk, metabolic disorders, insulin resistance, diabetes, systemic inflammation, etc.). In one embodiment, the patient may be diagnosed with increased overall sympathetic activity, and, in particular, conditions associated with central sympathetic overstimulation, such as hypertension, blood pressure variability, systemic inflammation, sleep disorders, anxiety and panic disorders, cardiovascular disease, history of stroke or TIA, obesity, metabolic syndrome, insulin resistance and diabetes, among others.

The system 10 includes an intravascular treatment device 12 operably coupled to an energy source or console 26 (e.g., a RF energy generator, a cryotherapy console). In the embodiment shown in FIG. 3, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may also include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise one or more irrigated electrodes.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The console 26 can be configured to deliver the treatment energy via an automated control algorithm 30 and/or under the control of the clinician. In addition, the console 26 may include one or more evaluation and/or feedback algorithms 31 to provide feedback to the clinician before, during, and/or after therapy.

The console 26 can further include a device or monitor that may include processing circuitry, such as a microprocessor, and a display 33. The processing circuitry may be configured to execute stored instructions relating to the control algorithm 30. The console 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

V. SELECTED EXAMPLES OF TREATMENT PROCEDURES FOR RENAL NEUROMODULATION

A. Achieving Intravascular Access to the Renal Artery

Figures 4A, 4B:
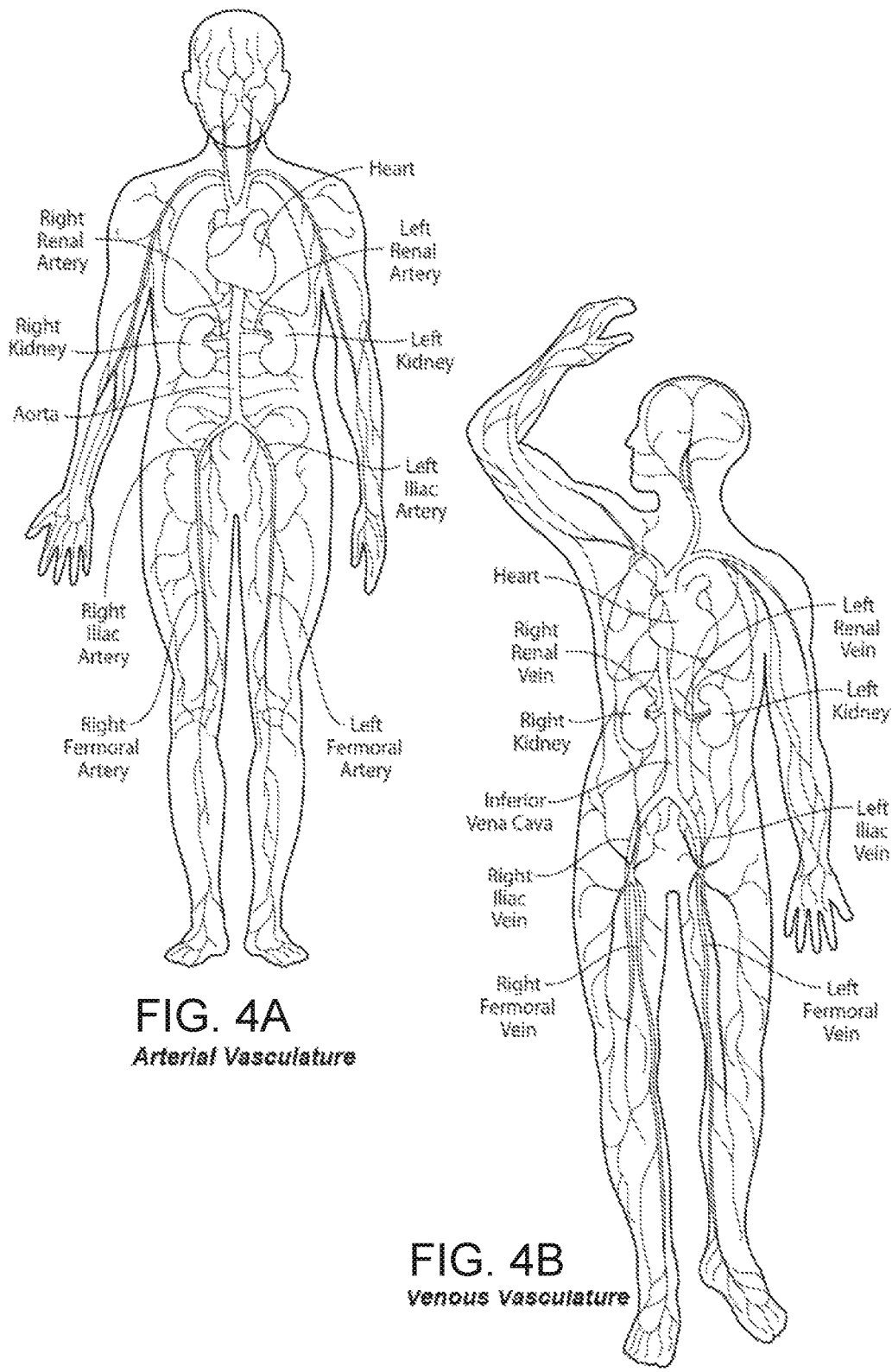
FIGS. 4A and 4B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

B. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, atherosclerosis, vascular disease, chronic inflammatory condition, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery. For example, spiral or helical CT technology can be used to produce 3D images of the vascular features for individual patients, and intravascular path choice as well as device size/diameter, length, flexibility, etc. can be selected based upon the patient's specific vascular features.

In addition to complicating renal arterial access, specifics of the renal anatomy also complicate establishment of stable contact between neuromodulatory apparatus and a luminal surface or wall of a renal blood vessel. When the neuromodulatory apparatus includes an energy delivery element, such as an electrode, transducer, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). To address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential lesion or ablation may outweigh the potential of renal artery stenosis or the risk may be mitigated with certain embodiments or in certain patients and creating a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

C. Neuromodulation of Renal Sympathetic Nerve at Treatment Site

Figure 5:
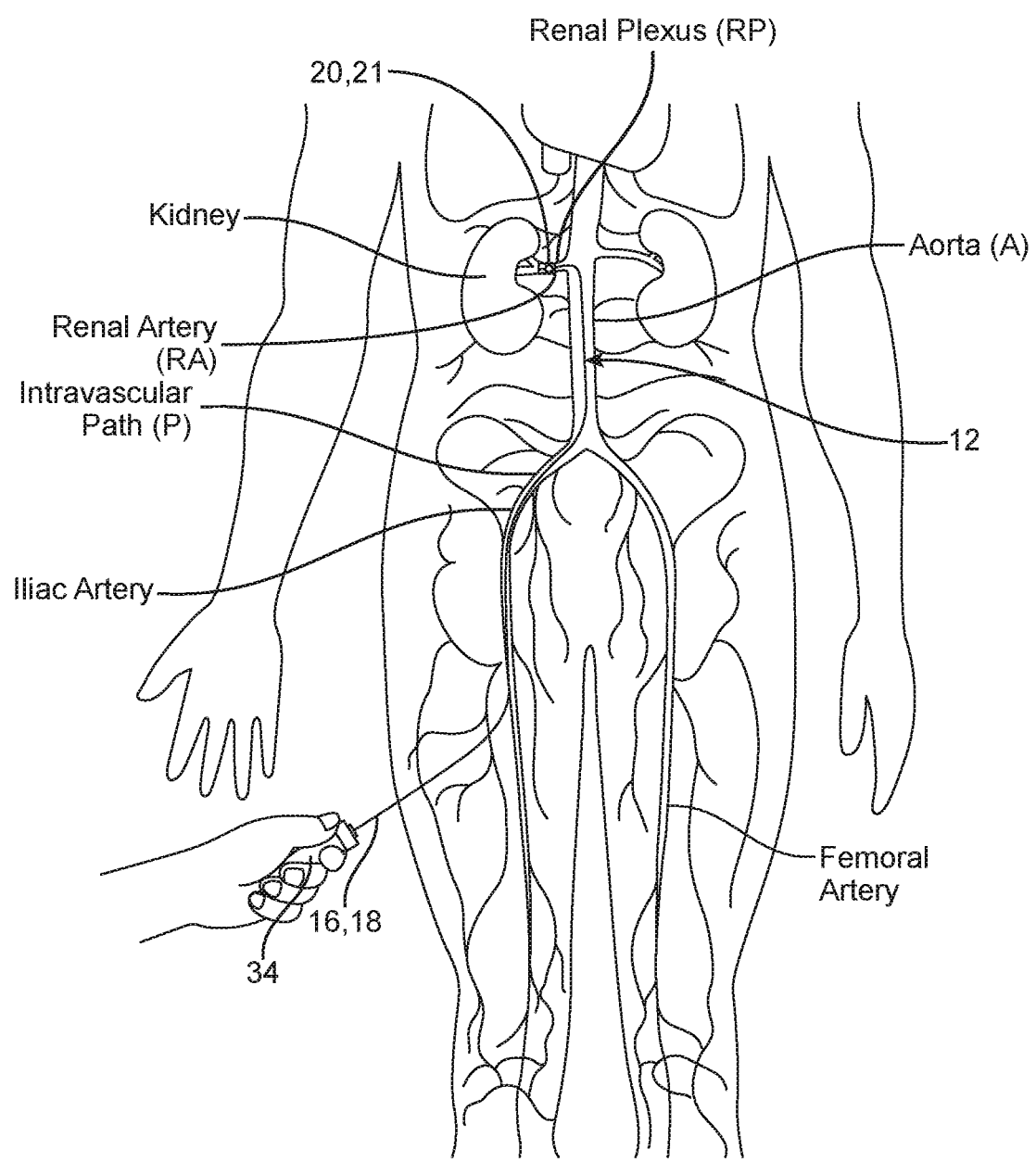
FIG. 5 illustrates modulating renal nerves with a neuromodulation system configured in accordance with an embodiment of the present technology.

FIG. 5 illustrates modulating renal nerves with an embodiment of the system 10 (FIG. 3). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., CT, fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured to form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively, or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Furthermore, a treatment procedure can include treatment at any suitable number of treatment locations, e.g., a single treatment location, two treatment locations, or more than two treatment locations. In some embodiments, the number of treatment locations receiving treatment in a renal artery can be 4-6 treatment locations, greater than 6 treatment locations, no less than 8 treatment locations, equal to or greater than 8 treatment locations, etc. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 6:
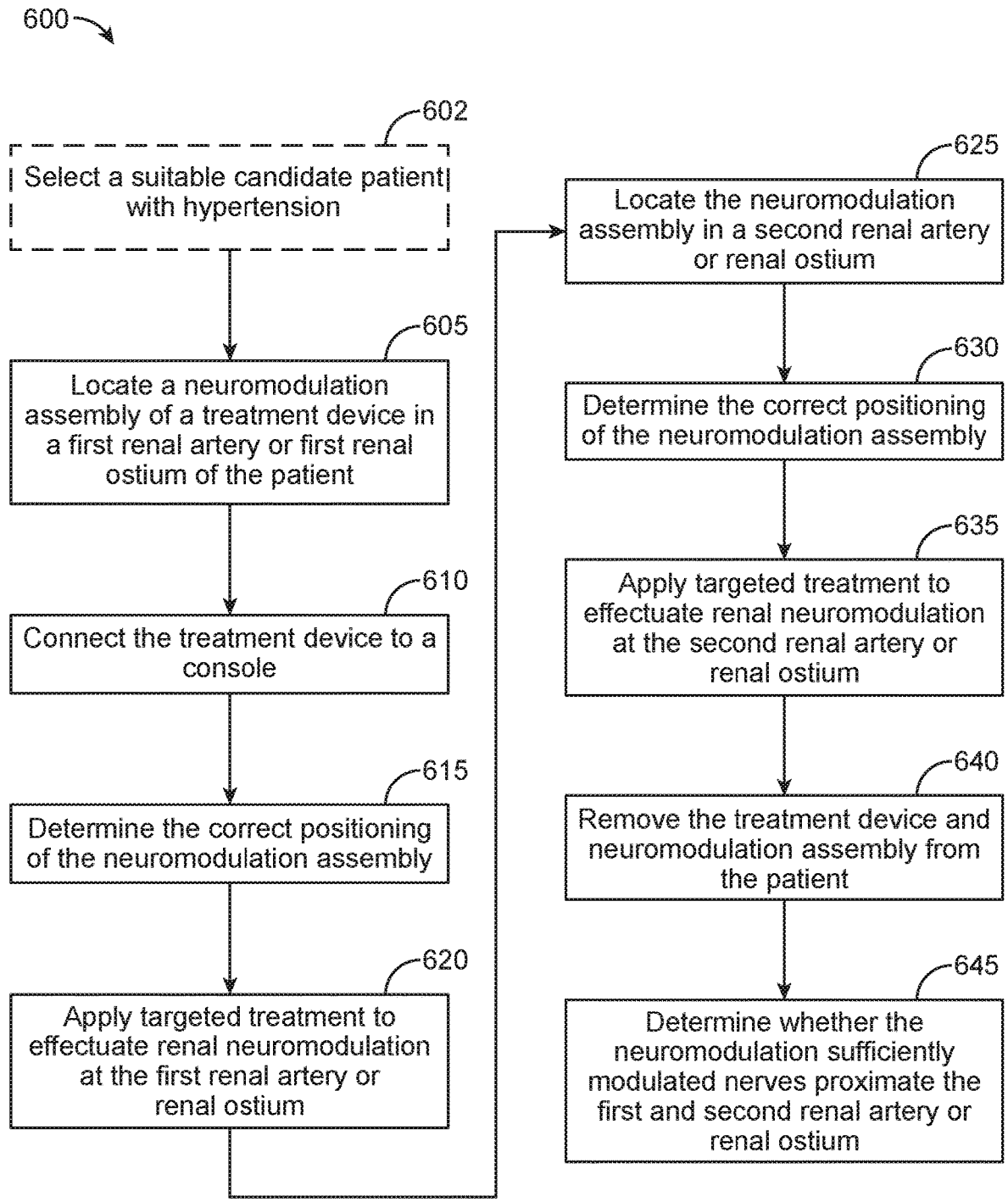
FIG. 6 is a block diagram illustrating a method of modulating renal nerves in accordance with an embodiment of the present technology.

FIG. 6 is a block diagram illustrating a method 600 of modulating renal nerves using the system 10 described above with reference to FIGS. 3 and 5. With reference to FIGS. 3, 5 and 6 together, the method 600 can optionally include selecting a suitable candidate patient having hypertension and an elevated heart rate (e.g., a 24-hour heart rate above a median heart rate of a population of hypertensive patients) for performing renal neuromodulation (block 602). For example, a suitable patient can include a patient having a systolic blood pressure above a threshold level, (e.g., at least 140 mm Hg, at least 145 mm Hg, at least 150 mm Hg) and a 24-hour ambulatory heart rate above a median heart rate for a population of hypertensive patients, a hypertensive patient having a 24-hour heart rate above 73 bpm, a prehypertensive patient having an elevated 24-hour heart rate and, optionally, one or more other risk factors associated with development of hypertension.

Modulating SNS nerves innervating the kidneys is expected to lower renal nerve activity and/or central SNS nerve activity, thereby inhibiting, preventing, slowing, disrupting or reversing physiological pathways associated with hypertension and/or lowering a risk associated with developing hypertension in the patient. In particular, targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing hypertension and/or symptoms associated with hypertension and/or conditions proposed to increase a patient's risk of developing hypertension and/or one or more comorbid medical conditions. Without being bound by theory, renal neuromodulation is anticipated to address the hyperactivity of the SNS and/or the elevated SNS tone present in patients with hypertension and/or patients having one or more risk factors of developing hypertension (e.g., severe hypertension, resistant hypertension, etc.).

The method 600 can include intravascularly locating the neuromodulation assembly 21 in a delivery state (e.g., low-profile configuration) to a first target site in or near a first renal blood vessel (e.g., first renal artery) or first renal ostium (block 605). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an OTW or a RX configuration). In some embodiments, radiopaque markers and/or markings on the treatment device 12 and/or the guide wire can facilitate placement of the neuromodulation assembly 21 at the first target site (e.g., a first renal artery or first renal ostium of the patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 600 can further include connecting the treatment device 12 to the console 26 (block 610), and determining whether the neuromodulation assembly 21 is in the correct position at the target site and/or whether the neuromodulation assembly (e.g., electrodes or cryotherapy balloon) is functioning properly (block 615). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 620).

In one example, the treatment device 12 can be an RF energy emitting device and RF energy can be delivered through energy delivery elements or electrodes to one or more locations along the inner wall of the first renal blood vessel or first renal ostium for predetermined periods of time (e.g., 120 seconds). In some embodiments, multiple treatments (e.g., 4-6) may be administered in both the left and right renal blood vessels (e.g., renal arteries) to achieve a desired coverage and/or desired inhibition of sympathetic neural activity in the body.

In some embodiments, a treatment procedure can include applying a suitable treatment modality at a treatment location in a testing step (not shown) followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would lesion a nerve (e.g., about 65° C.). A clinical objective of the procedure typically is to treat (e.g., lesion) a sufficient number of renal nerves (either efferent or afferent nerves) to cause a reduction in sympathetic tone or drive to the kidneys. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

In a specific example of using RF energy for renal nerve modulation, a clinician can commence treatment which causes the control algorithm 30 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the neuromodulation assembly 21). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can then be located at a second target site in or near a second renal blood vessel (e.g., second renal artery) or second renal ostium (block 625), and correct positioning of the assembly 21 can be determined (block 630). In selected embodiments, a contrast material can be delivered distally beyond the neuromodulation assembly 21 and fluoroscopy and/or other suitable imaging techniques can be used to locate the second renal artery. The method 600 continues by applying targeted heat or cold to effectuate renal neuromodulation at the second target site to cause partial or full denervation of the kidney associated with the second target site (block 635).

After providing the therapeutically-effective neuromodulation energy (e.g., cryogenic cooling, RF energy, ultrasound energy, etc.), the method 600 may also include removing the treatment device 12 (e.g., catheter) and the neuromodulation assembly 21 from the patient (block 640). In some embodiments, the neuromodulation assembly 21 can be an implantable device (not shown) and a treatment procedure can include implanting the neuromodulation assembly 21 at a suitable treatment location within the selected patient. Other treatment procedures for modulation of target sympathetic nerves in accordance with embodiments of the present technology are also possible.

The method 600 may also include determining whether the neuromodulation sufficiently modulated nerves or other neural structures proximate the first and second target sites (block 645). For example, the process of determining whether the neuromodulation therapeutically treated the nerves can include determining whether nerves were sufficiently modulated or otherwise disrupted to reduce, suppress, inhibit, block or otherwise affect the afferent and/or efferent renal signals (e.g., by evaluation of suitable biomarkers, stimulation and recording of nerve signals, etc.). Examples of suitable biomarkers and their detection are described in International Patent Application No. PCT/US2013/030041, filed Mar. 8, 2013, and International Patent Application No. PCT/US2015/047568, filed Aug. 28, 2015, the disclosures of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety.

In a further embodiment, patient assessment could include determining whether the neuromodulation therapeutically treated the patient for hypertension Assessment of certain suitable biomarkers and/or nerve signals may be made immediately or shortly after neuromodulation (e.g., about 15 minutes, about 24 hours, or about 7 days post-neuromodulation). In further embodiments, patient assessment could be performed at time intervals (e.g., about 1 month, 3 months, 6 months, 12 months) following neuromodulation treatment. For example, the patient can be assessed for measurements of blood pressure, 24-hour ambulatory heart rate, blood pressure variability, nocturnal blood pressure "dipping", MSBP level, skin conductance, resting heart rate, sleep patterns or quality, measures of sympathetic activity (e.g., MSNA, renal and/or total body norepinephrine spillover, plasma norepinephrine levels, and heart rate variability), peripheral inflammatory markers (e.g., IL-6, CRP, etc.), NPY level, measures of HPA axis function (e.g., glucocorticoid levels (e.g., in hair, urine, plasma, etc.), glucocorticoid resistance, CAR level, CRH level, etc.), sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, and/or markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio).

In other embodiments, various steps in the method 600 can be modified, omitted, and/or additional steps may be added. In further embodiments, the method 600 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place a second treatment session at a later time.

VI. EXPERIMENTAL EXAMPLES

The following section provides some limiting examples of methods for treating hypertension.

Example 1

Study Design in Patients

The rationale and study design of SPYRAL HTN-OFF MED (clinicaltrials.gov: NCT02439749) has been described elsewhere (Kandzari D E, et. al., Am Heart J, 2016; 171: 82-91). In brief, SPYRAL HTN-OFF MED was a multicentre, international, single-blinded, randomized sham-controlled proof of concept trial enrolling patients aged 20-80 years with mild to moderate hypertension. Inclusion criteria were an office systolic blood pressure (SBP)≥150 mmHg and <180 mmHg, office diastolic blood pressure (DBP)≥90 mmHg and a mean 24-hour ambulatory SBP≥140 mmHg and <170 mmHg. Patients were enrolled in the United States (10 centres), Germany (4 centres), Japan (2 centres), United Kingdom (2 centres) and Australia, Austria and Greece (1 centre each). The trial complies with the Declaration of Helsinki, local ethics committees of all centres approved the research protocol and written informed consent was obtained from all patients.

Blinding and Randomization

Patients were assigned either to renal denervation or sham procedure by a 1:1 randomization. Randomization was done by Icon PLC by use of SAS based software to generate lists of randomization codes. Before randomization, patients were required to be off all anti-hypertensive medication. An initial screening visit was done to verify eligibility criteria and initiate medication washout if needed. After a 3-4 week washout period blood pressure levels were confirmed to determine patient eligibility for randomization. All patients' urine and plasma were evaluated for the absence of anti-hypertensive medication by use of tandem high performance liquid chromatography and mass spectrography by an independent laboratory. Office blood pressure and heart rate measurements were obtained with an automated blood pressure monitor (Omron, Omron Health Care Inc., Lake Forest, Ill., US). 24-hour ABPM (Mobil-O-Graph I.E.M. GmbH, Stolberg, Germany) was applied to evaluate blood pressure and heart rate over 24 hours. Blood pressure and heart rate was taken every 30 minutes and only patients with at least 21 daytime and 12 night-time measurements were included in the final analysis.

Intervention

Patients were not informed of their randomization and were scheduled for eligibility by renal angiogram. If anatomically suitable, patients were randomized to renal denervation or the sham procedure. During this procedure, patients were blinded by a combination of sensory isolation (blindfolding and music) and conscious sedation. Patients were not familiar with procedural details and duration of the angiogram. Physicians and designated staff were blinded during the angiogram until randomization and assignment to the respective treatment arm. All follow-up visits were performed by blinded staff and referring physicians were not informed of the treatment allocation. The blinding score was determined by asking patients to guess which randomization group they were allocated to at discharge and at three months.

Radiofrequency ablation treatments were performed using the Symplicity Spyral™ multi-electrode catheter (Medtronic) and the Symplicity G3™ generator (Medtronic). This catheter allows circumferential ablation treatments in a spiral pattern in all four quadrants of vessels greater than 3 mm and less than 8 mm. All interventionalists had previous experience with renal denervation and completed a structured proctoring programme. With this approach, all accessible renal arteries including branch vessels and accessory arteries were targeted. A renal angiogram was performed in the control group and patients remained on the table for at least 20 minutes to prevent unblinding.

Blood Pressure and Heart Rate Effects

The primary efficacy outcome was blood pressure reduction based on ABPM measurements at three months, which was not a prespecified endpoint but an example physiological measure. In this example, the effects of renal denervation on heart rate are examined at different day and night-time periods. Daytime and night-time periods in this analysis were defined as 9:00 AM to 8:59 PM and 1:00 to 5:59 AM, respectively. Specific parameters were defined as follows: average morning heart rate as average heart rate measured between 7:00-8:59 AM, moving peak morning heart rate as highest one hour moving average of ≥3 consecutive heart rate measurements between 6:00 and 9:59 AM, average morning heart rate surge as average morning heart rate minus average night-time heart rate, average peak night-time heart rate as average of 3 highest heart rate measurements during the night-time, moving lowest night heart rate as lowest 1-hour moving average of ≥3 consecutive night-time heart rate measurements, and average night-time heart rate surge as average peak night-time heart rate minus average night-time heart rate. Then, groups were separated by average 24-hour heart rate above and below the median (median=73.5 bpm) and the blood pressure responses for average 24-hour, average daytime, average night-time SBP and DBP were evaluated. In addition, morning average, maximum and minimum SBP were evaluated in the two heart rate groups.

Night-time heart rate fall (%) was calculated as $100*[1-HR_{PM}/HR_{AM}]$, where $HR_{PM}$ is mean night-time heart rate and $HR_{AM}$ is mean daytime heart rate. Patients were classified as extreme dippers if night-time heart rate fall was >20%, dippers had a drop ≥10% and <20%, non-dippers had a drop ≥0% and <10%, and reverse dippers had a drop <0%.

Statistical Analysis

Statistical analysis was performed according to the intention to treat principle. Means and standard deviations of continuous variables are presented per treatment group. Analysis of Covariance (ANCOVA) was employed to adjust for baseline blood pressure measurements. Between group differences were tested with unpaired T-tests and differences between baseline and a 3-months follow-up assessment test with paired T-tests. Comparison of treatment groups for categorical variables were tested with the exact test for binary variables and the Chi square test for multilevel categorical variables. Interaction testing between baseline 24-hour heart rate and treatment effect on 3 month outcomes was also conducted. SAS (version 9.2) was used for all statistical analyses.

Results

The first results of SPYRAL HTN-OFF MED were generated in 38 patients after renal denervation and 42 patients after sham procedure. Table 1 summarizes the baseline patient characteristics. There were no statistical differences according to baseline characteristics. Patients were overweight and had low prevalence of comorbidities like diabetes type 2, obstructive sleep apnea, peripheral artery disease, coronary disease, history of stroke and transient ischemic attack or acute coronary syndrome. Blinding was successfully achieved, and the majority of patients adhered to the protocol and had no evidence of anti-hypertensive medication used in the toxicological analysis at baseline and after three months.

TABLE 1

Baseline demographics

| Mean ± SD or % (N) | RDN (N = 38) | Sham control (N = 42) |
|---|---|---|
| Age (years) | 55.8 ± 10.1 | 52.8 ± 11.5 |
| Male | 68.4% (26) | 73.8% (31) |
| BMI (kg/m$^2$) | 29.8 ± 5.1 | 30.2 ± 5.1 |
| Body weight (kg) | 88.8 ± 16.6 | 90.9 ± 19.1 |
| Diabetes type 2 | 2.6% (1) | 7.1% (3) |
| Current smoker | 10.5% (4) | 23.8% (10) |
| Obstructive sleep apnea | 7.9% (3) | 7.1% (3) |
| Peripheral artery disease | 2.6% (1) | 0.0% (0) |
| Coronary artery disease* | 0.0% (0) | 4.8% (2) |
| Stroke and transient ischemic attack* | 2.6% (1) | 0.0% (0) |
| Myocardial infarction/acute coronary syndrome* | 0.0% (0) | 2.4% (1) |

BMI: body mass index;
RDN: renal denervation;
SD: standard deviation
*These events occurred >3 months before randomization.
P = NS for differences in all baseline characteristics.

Mean 24-hour heart rate, SBP, and DBP measurements were similar at baseline (Table 2). Changes in 24-hour heart rate and DBP at 3 months were significantly different for the renal denervation group compared to sham and trended toward greater reduction for SBP (Table 2).

TABLE 2

24-hour heart rate and blood pressure measurements at baseline and 3 months, and changes at 3 months

| | Baseline | | 3 Months | | Change at 3 months | | |
|---|---|---|---|---|---|---|---|
| | RDN (N = 35) | Sham (N = 36) | RDN (N = 35) | Sham (N = 36) | RDN (N = 35) | Sham (N = 36) | Mean Difference: RDN vs. Sham[1] |
| 24-hour HR (bpm) | 72.9 ± 11.0 | 74.4 ± 11.7 | 70.4 ± 8.5 | 74.2 ± 9.6 | −2.5 ± 5.3 [−4.3, −0.7] | −0.2 ± 4.1 [−1.5, 1.2] | −2.7 [−4.5, −1.0] p = 0.003 |
| 24-hour SBP (mmHg) | 153.5 ± 9.2 | 152.3 ± 7.6 | 148.0 ± 10.8 | 151.8 ± 11.1 | −5.5 ± 10.3 [−9.1, −2.0] | −0.5 ± 10.1 [−3.9, 2.9] | −4.6 [−9.2, 0.1] p = 0.053 |
| 24-hour DBP (mmHg) | 99.6 ± 7.4 | 98.9 ± 8.3 | 94.8 ± 8.3 | 98.5 ± 9.9 | −4.8 ± 6.4 −7.0, −2.6] | −0.4 ± 5.4 [−2.2, 1.4] | −4.3 [−7.1, −1.5] p = 0.003 |

Bpm: beats per minute;
DBP: diastolic blood pressure;
HR: heart rate;
RDN: renal denervation;
SBP: systolic blood pressure
Data presented as mean ± standard deviation.
[1]P-value from ANCOVA model, adjusting for baseline heart rate or blood pressure.

Figure 7:
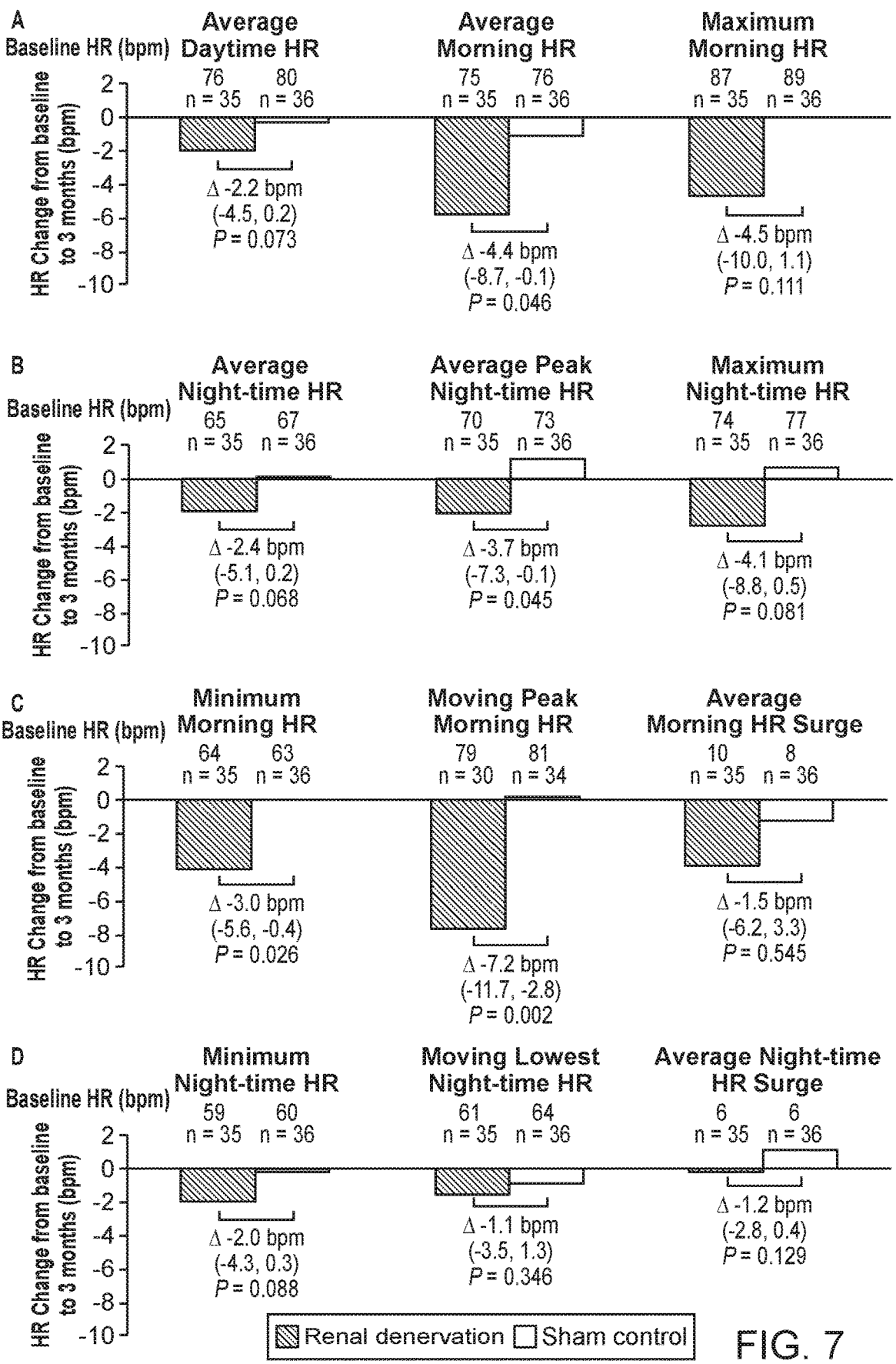
FIG. 7 shows changes in 24-hour heart rate (HR) after renal denervation or sham treatment on average daytime HR, average morning HR and maximum morning HR (Panel A); average night-time HR, average peak night-time HR and maximum night-time HR (Panel B); minimum morning HR, moving peak morning HR and average morning HR surge (Panel C) and minimum night-time HR, moving peak night-time HR and average night-time HR surge (Panel D). Treatment differences, 95% confidence intervals and p-values were calculated from ANCOVA model, adjusting for baseline blood pressure.

There was a nominal decrease in average daytime heart rate and maximum morning heart rate, while average morning heart rate was significantly reduced compared to sham (FIG. 7, Panel A). Average night-time and maximum night-time heart rate were not significantly reduced, but a significant difference between groups was observed for average peak night-time HR (FIG. 7, Panel B). FIG. 7, Panel C shows a significant reduction and intergroup difference in the minimum morning heart rate and moving peak morning heart rate. The difference between groups for the average heart rate surge was not statistically significant (FIG. 7, Panel C). Likewise, moving lowest and minimum night-time heart rate and average night-time surge were numerically but not significantly different.

Figure 8:
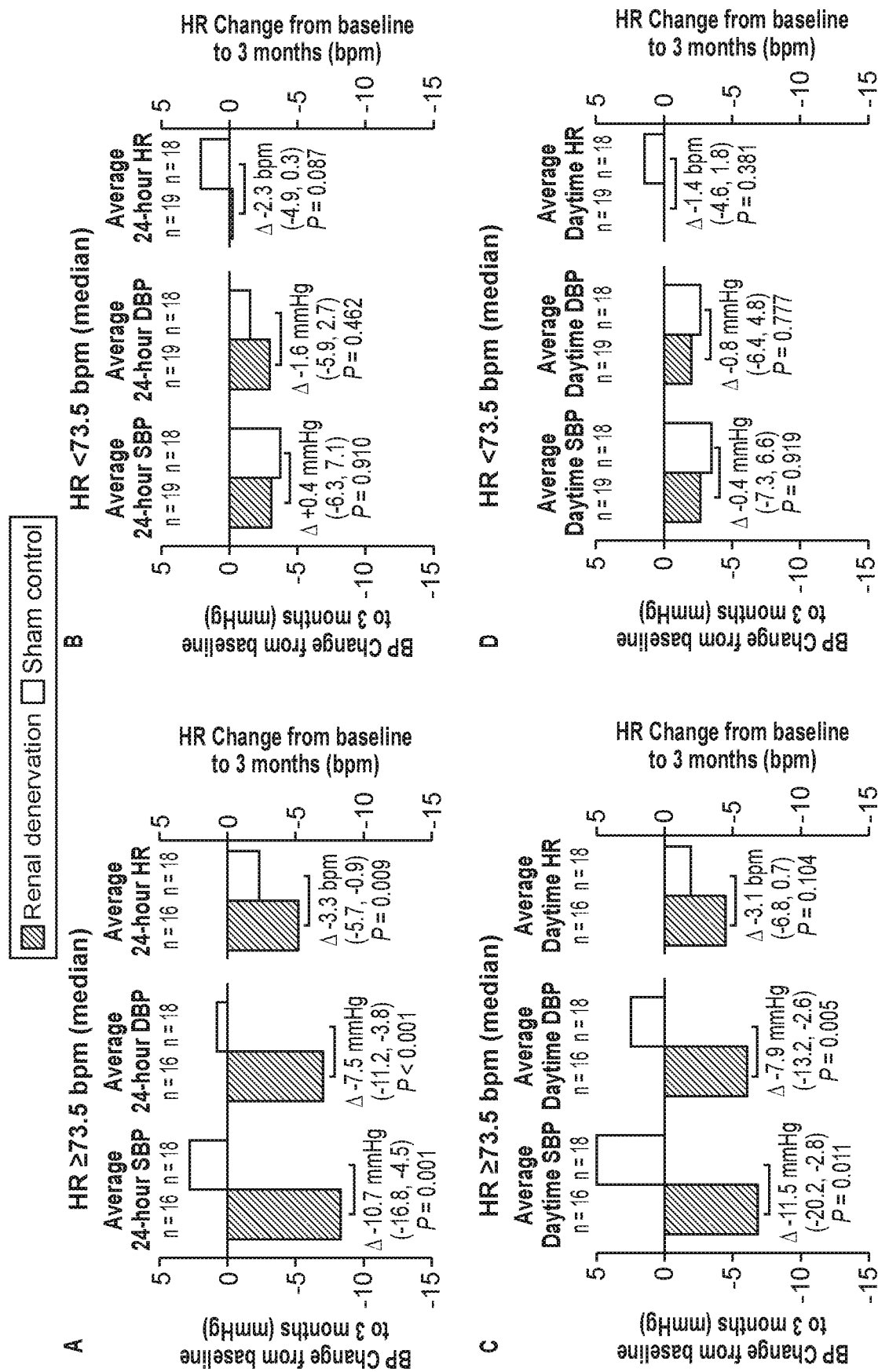
FIG. 8 shows changes in heart rate (HR) and blood pressure (BP) from baseline to 3 months comparing patients with baseline 24-hour HR above and below the median (73.5 bpm). Treatment differences, 95% confidence intervals and p-values were calculated from ANCOVA model, adjusting for baseline blood pressure. P-values calculated from interaction testing ($P_{int}$) between baseline 24-hour HR and treatment effect for each 3-month outcome are included. Panels (A) and (B) compare average 24-hour systolic BP ($P_{int}$=0.028), diastolic BP ($P_{int}$=0.044) and HR ($P_{int}$=0.306). Panels (C) and (D) compare average daytime systolic BP ($P_{int}$=0.029), diastolic BP ($P_{int}$=0.015) and HR ($P_{int}$=0.398). Panels (E) and (F) compare average night-time systolic BP ($P_{int}$=0.049), diastolic BP ($P_{int}$=0.205) and HR ($P_{int}$=0.842).
Figure 8:
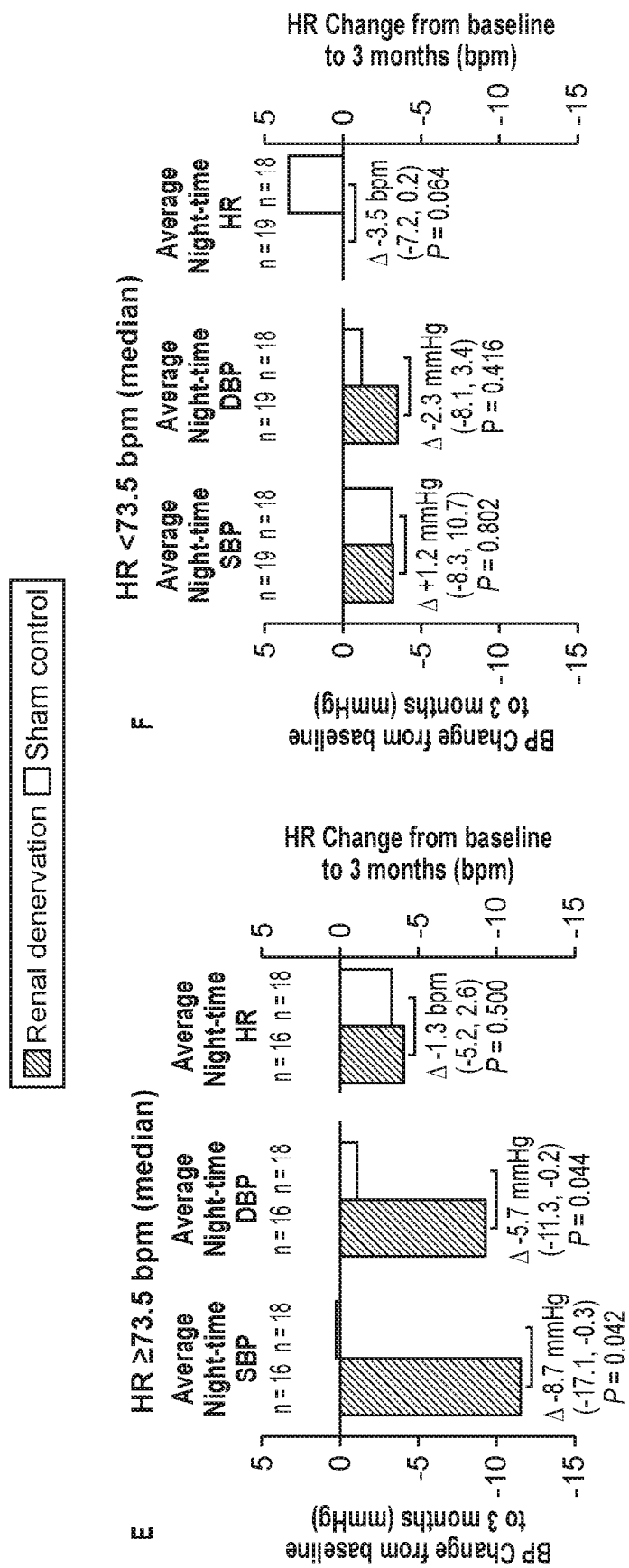
Figure 9:
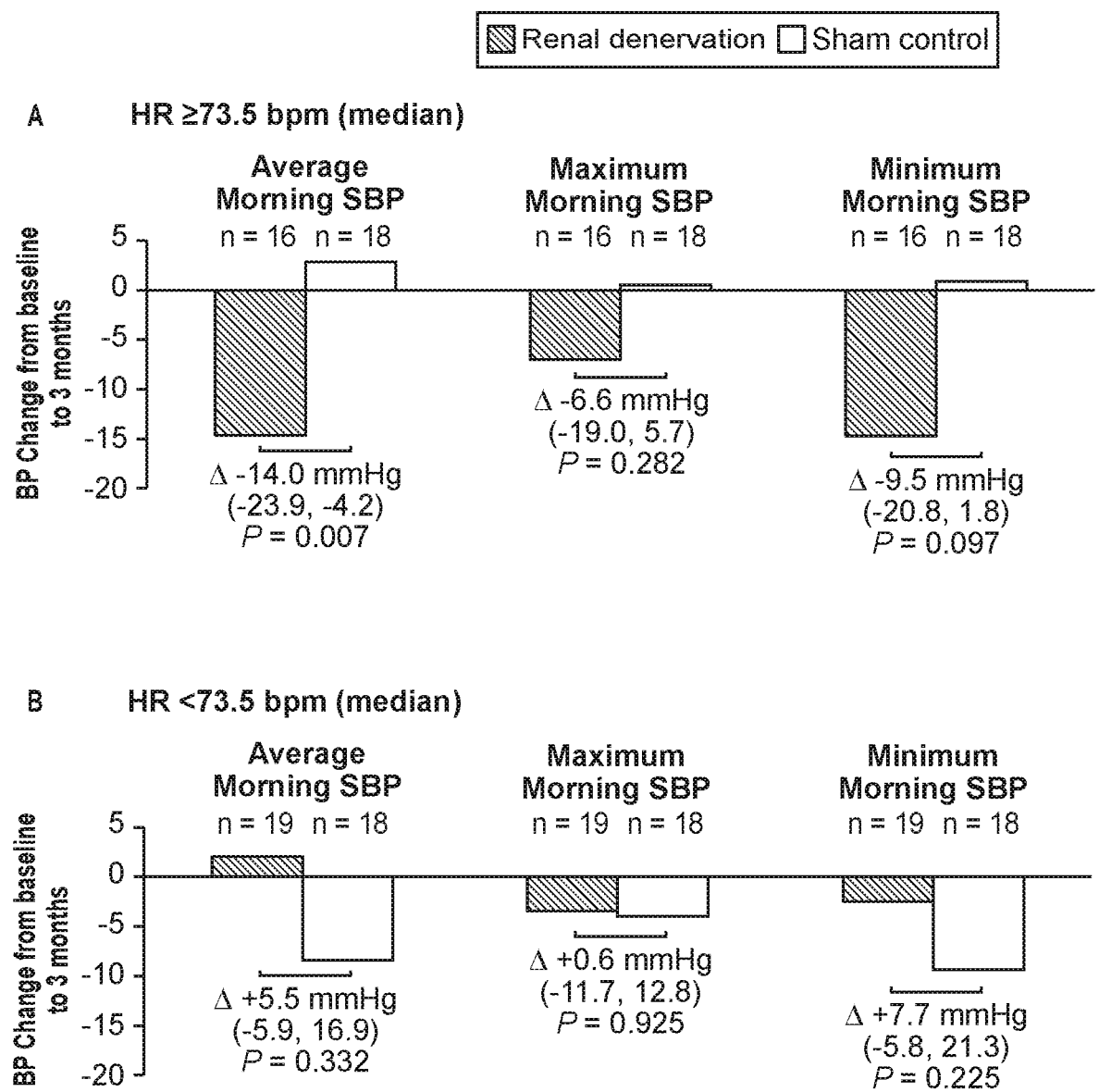
FIG. 9 shows changes in morning systolic blood pressure (SBP) from baseline to 3 months comparing patients with baseline 24-hour heart rate above and below the median (73.5 bpm). Treatment differences, 95% confidence intervals and p-values were calculated from ANCOVA model, adjusting for baseline blood pressure. P-values calculated from interaction testing ($P_{int}$) between baseline 24-hour heart rate and treatment effect for each 3-month outcome are included.

Given that increased sympathetic tone impacts heart rate and renal denervation is hypothesized to impact systemic and sympathetic tone, an analysis was done to see if baseline heart rate predicts the response of renal denervation to both heart rate and blood pressure. The populations were separated into those with a 24-hour baseline heart rate above and below the median (≥ or <73.5 bpm). FIG. 8, Panel A shows that for a heart rate above the median, there was a significant reduction of average 24-hour SBP, average 24-hour DBP and average 24-hour heart rate for the renal denervation group compared to sham. These reductions were greater compared to the subgroups with a heart rate below the median (<73.5 bpm), where no statistical intergroup differences were observed (FIG. 8, Panel B). Similar results were obtained for average daytime SBP and DBP (FIG. 8, Panel C) and average night-time SBP and DBP (FIG. 8, Panel E) with significant reductions after renal denervation in the group with baseline 24-hour heart rate above the median. Compared to the group with lower 24-hour baseline heart rates (<73.5 bpm median), no differences in average daytime SBP, DBP or heart rate (FIG. 8, Panel D) or night-time SBP, DBP or heart rate (FIG. 8, Panel F) were observed. Finally, the average morning SBP was significantly reduced only at a heart rate above the median (FIG. 9, Panel A), but not below (FIG. 9, Panel B).

In order to explore whether the average office blood pressure response was different according to average 24-hour baseline heart rate, the average office SBP changes from baseline to three months were assessed. There was a significant difference between renal denervation and sham groups at heart rates above the median (>73.5 bpm), but not for patients with heart rates below the median (FIG. 10). Changes in 24-hour, morning, daytime and night-time heart rate at three months for individual patients in renal denervation and sham groups are shown in FIG. 11. Overall, the dipping patterns of heart rate did not change after renal denervation (Table 3).

hypertensive medications (Townsend R R, et. al., Lancet, 2017; 390:2160-2170). Therefore, neither the effect of blood pressure reduction nor the effect of other physiological parameters of sympathetic activation like heart rate is confounded by the effects of drugs. As reported herein, renal denervation reduces heart rate measured during ABPM with a different effect at various times of the day. Significant reduction of heart rate was observed in the morning with significant reductions of the peak morning heart rate and average morning heart rate surge. As demonstrated in this example, patients with baseline 24-hour heart rate above the median had greater reductions in 24-hour mean, daytime and night-time blood pressure following renal denervation. As such, a higher baseline heart rate may predict neurogenic hypertension and, in one embodiment, can be used to identify hypertensive patients suitable for renal denervation treatment.

In previous studies, including a large single-centre registry (Ukena C, et al., Int J Cardiol, 2013; 167:2846-2851) and the Global Symplicity Registry (Bohm M, et al., J Hypertens, 2016; 34:2480-2486), heart rate was not predictive of blood pressure reduction by renal denervation. However, as demonstrated in this example, in patients with a heart rate above the median as a potential sign of sympathetic activation, higher heart rate was predictive of reduction in average daytime SBP, daytime DBP and office SBP.

Further, the analysis of 24-hour heart rate on the differential effects of sympathetic modulation on heart rate profiles demonstrated differences as shown herein. While there was a significant reduction of heart rate in the morning hours and during daytime, there was no significant effect on heart

TABLE 3

Ambulatory heart rate dipper[1] status at baseline and 3 months

| | Baseline | | 3 months | | |
|---|---|---|---|---|---|
| | RDN (N = 37) | Sham (N = 42) | RDN (N = 36) | Sham (N = 36) | Mean Difference: RDN vs. Sham[2] |
| Extreme Dipper | 16.2% (6/37) | 9.5% (4/42) | 16.7% (6/36) | 11.1% (4/36) | 5.6% [−18.7%, 29.3%] p = 0.735 |
| Dipper | 37.8% (14/37) | 59.5% (25/42) | 41.7% (15/36) | 55.6% (20/36) | −13.9% [−37.1%, 10.5%] p = 0.346 |
| Non-Dipper | 40.5% (15/37) | 21.4% (9/42) | 36.1% (13/36) | 22.2% (8/36) | 13.9% [−10.5%, 37.1%] p = 0.300 |
| Reverse Dipper | 5.4% (2/37) | 9.5% (4/42) | 5.6% (2/36) | 11.1% (4/36) | −5.6% [−29.3%, 18.7%] p = 0.674 |

RDN: renal denervation
[1]Night-time heart rate fall (%) was calculated as $100*[1 - HR_{PM}/HR_{AM}]$, where $HR_{PM}$ is mean night-time heart rate and $HR_{AM}$ is mean daytime heart rate. Patients were classified as extreme dippers if night-time heart rate fall was >20%, dippers had a drop ≥10% and <20%, non-dippers had a drop ≥0% and <10%, and reverse dippers had a drop <0%.
[2]P-value compares dipper status of RDN vs. Sham groups at 3 months.

DISCUSSION

Renal denervation therapy has been shown to reduce blood pressure in open studies (Esler M D, et. al., Eur Heart J, 2014; 35:1752-1759; Krum H, et. al., Lancet, 2014; 383:622-629), two randomized studies (Azizi M, et. al., Lancet, 2015; 385:1957-1965; Rosa J, et. al., Hypertension, 2015; 65:407-413) and one randomized sham-controlled trial (Desch S, et. al., Hypertension, 2015; 65:1202-1208) as well as one real-world registry involving more than 2000 patients (Bohm M, et. al., Hypertension, 2015; 65:766-774). The recently published randomized, sham-controlled SPYRAL HTN-OFF MED trial provided the biological proof of principle that catheter-based renal denervation can reduce blood pressure in hypertensives without any antirate at night. Furthermore, the lowest heart rates in the morning were more reduced than higher heart rates at daytime. Without being bound by theory, this example suggests that renal denervation may act in part by decreasing basal sympathetic activity, while still maintaining the capacity to activate the sympathetic nervous system during activity or in response to stimulus. This is in agreement with exercise studies showing that blood pressure and heart rate are reduced, not only on exercise but also at rest. However, the increase of heart rate and blood pressure during exercise has not been shown to be affected by catheter-based renal denervation treatment for hypertension.

Heart rate has previously been shown to be a predictor of cardiovascular outcomes in various cardiovascular and non-cardiovascular conditions, including in the general population, in hypertension, in high-risk vascular patients after stroke or myocardial infarction and in heart failure. Diagnostic data from implantable cardiac devices such as high night-time heart rate has been associated with a higher risk of heart failure readmission. Also, night-time and morning blood pressures have been shown to be more significantly associated with cardiovascular outcomes compared to average 24-hour SBP or average daytime SBP. This example demonstrated a particular reduction in morning heart rates after renal denervation with the same association existing for BP.

Example 2

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter commercially available from Medtronic, Inc., of 710 Medtronic Parkway, Minneapolis, Minn. 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 3

Example 2 describes the outcome of catheter-based renal neuromodulation on human patients diagnosed with hypertension. Patients selected having a baseline systolic blood pressure of 160 mm Hg or more and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, p<0.0001), whereas they did not differ from baseline in the control group (change of 1/0 mm Hg, baseline of 178/97 mm Hg, p=0.77 systolic and p=0.83 diastolic). Between-group differences in blood pressure at 6 months were 33/11 mm Hg (p<0.0001). At 6 months, 41 (84%) of 49 patients who underwent renal neuromodulation had a reduction in systolic blood pressure of 10 mm Hg or more, compared with 18 (35%) of 51 control patients (p<0.0001).

Example 4

Example 3 describes the outcome of catheter-based renal neuromodulation on animal subjects in an additional experiment. In this example (and referring to FIGS. 12A and 12B), studies using the pig model were performed using a multi-electrode Symplicity Spyral™ catheter or a single-electrode Symplicity Flex™ catheter along with a Symplicity G3™ generator. The catheters and generator are commercially available from Medtronic, Inc. The catheters were used in these cohorts of animals (n=66) to create multiple RF ablations in the renal vasculature. Cortical axon density in the renal cortex (FIG. 12A) and renal cortical norepinephrine (NE) concentration (FIG. 12B) were used as markers to measure procedural efficacy.

As shown in FIG. 12A, cortical axon area (per $mm^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

FIG. 12B includes (a) a graph of normalized cortical axon area vs. renal NE concentration, and (b) a graph of renal NE concentration vs. extent (%) of nerve ablation. Referring to the table of FIG. 12A and the two graphs of FIG. 12B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 12B, which demonstrates that a decrease in cortical axon area correlates with a decrease in NE levels. Referring to the second graph of FIG. 12B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 5

Example 4 describes an example of the outcome of renal neuromodulation on human patients. Markers of cardiovascular inflammation and remodeling were assessed (Dörr, O., et al., *Clin Res Cardiol*, 2015, 104: 175-184). A total of 60 patients (mean age of 67.9±9.6 years) diagnosed with resistant arterial hypertension were treated with percutaneous, catheter-based renal sympathetic denervation. Treatment included RF energy delivery to the renal artery using a Symplicity® catheter system commercially available from Medtronic, Inc. In this human trial, a therapeutic response was defined as a systolic blood pressure (BP) reduction of >10 mmHg in the office blood pressure measurement 6 months after renal denervation. Of the 60 patients, 49 patients (82%) were classified as responders with a mean systolic BP reduction of >10 mmHg. Venous blood samples for determination of biomarkers of inflammation (e.g., IL-6, high-sensitive C-reactive protein (hsCRP)) and markers of vascular remodeling (matrix metalloproteinases (MMP-2 and MMP-9), tissue inhibitors of matrix metalloproteinases (TIMP-1)) were collected at baseline (prior to renal denervation) and 6 months after renal denervation for all patients.

Collected data from all patients demonstrated that bilateral renal nerve denervation resulted in a significant reduction in mean office systolic BP of 26.4 mmHg (169.3±11.3 mmHg at baseline vs. 142.9±13.8 mmHg at follow-up; p<0.001). The procedure further resulted in a significant reduction in the serum levels of hsCRP (3.6 mg/dL at baseline vs. 1.7 mg/dL at follow-up, p<0.001), and a significant reduction in the pro-inflammatory cytokine IL-6 (4.04 pg/mL at baseline vs. 2.2 pg/mL at follow-up, p<0.001) six months after treatment. Additionally, the procedure resulted in a significant increase in the serum levels of MMP-9 (425.2 ng/mL at base line vs. 574.1 ng/mL at follow-up, p=0.02), and in serum levels of MMP-2 (192.3 ng/mL at baseline vs. 231.3 ng/mL at follow-up, p<0.001). There were no significant changes in TIMP-1 6 months after renal denervation. Notably, of non-responders (e.g., patients with a BP reduction of <10 mmHg), serum levels of hsCRP still decreased (3.2 mg/dL at baseline vs. 2.4 mg/dL at follow-up, p=0.09), and serum levels of 1-6 still decreased (3.1 pg/mL at baseline vs. 2.7 pg/mL at follow-up, p=0.16), although there was a significantly greater beneficial effect of renal denervation on biomarker levels in BP responders when compared with non-responders.

These findings suggest that catheter-based renal neuromodulation exhibits a positive vascular and systemic effect on mediators of inflammation, IL-6 and hsCRP, and inhibitors (MMP-9 and MMP-2) of deleterious cardiovascular remodeling. Low serum levels of MMP-9 and MMP-2 have been found to be essential to damaging vascular remodeling found in essential hypertension and progression of end-organ damage These findings suggest that levels of MMP-9 and MMP-2, which are involved in ECM turnover in different tissues, including the arterial wall, can be elevated post-renal neuromodulation, and, without being bound by theory, are postulated to be beneficial in reversal of damage to the vessels caused by inflammation, cardiovascular disease and/or hypertension. In addition to lowering systolic BP in (responsive) hypertensive patients, these findings suggest that renal denervation has a positive effect on biomarkers of inflammation (e.g., IL-6, hsCRP) and cardiovascular remodeling (e.g., MMP-2, MMP-9) separate from and in addition to the effect on blood pressure.

Example 6

Example 5 describes an example of the effects of renal neuromodulation on nocturnal blood pressure using ambulatory 24-hour blood pressure (BP) monitoring in human patients. Elevated blood pressure during the night-time as well as early morning hours (e.g., elevated morning surge in BP; "MSBP") is associated with an increased risk of cardiovascular events and strokes. In this example, a total of 576 patients diagnosed with resistant arterial hypertension (e.g., baseline office systolic BP≥160 mm Hg and 24-hour ambulatory systolic BP≥135 mm Hg) were either treated ("RDN treated"; n=382) with bilateral percutaneous, catheter-based renal sympathetic denervation (mean age of 58±11 years) or blindly treated ("blind control"; n=159) with a sham procedure (e.g., renal angiogram) or not treated ("control"; n=19) (Kario, K., et al., *Hypertension*, 2015, 66:1130-1137). Treatment included RF energy delivery to the renal artery using a Symplicity™ catheter system (Medtronic, Inc.). The renal neuromodulation ("RDN") treated group received up to six ablations rotated in 45 degree increments and approximately 5 mm apart for 2 minutes each in both renal arteries. Treatments were delivered from the first distal main renal artery bifurcation to the ostium proximally and were spaced longitudinally and rotationally under fluoroscopic guidance. BP variability, morning ambulatory, night-time ambulatory and daytime ambulatory systolic BP was measured by 24-hour ambulatory BP monitoring before renal denervation and at 6 months after renal denervation.

In patients with resistant hypertension, renal denervation resulted in significant reduction in ambulatory night-time and morning BP. For example, mean ambulatory night-time BP measurements in the RDN treated group were reduced by 6.3±18.2 mm Hg (p<0.001; baseline of 151.5±18.3 mm Hg, p=0.24), whereas they were not significantly reduced (−1.7±19.2 mm Hg; p=0.233) from baseline (149.5±20.1 mm Hg, p=0.24) in the blind control+control group 6 months post-neuromodulation. Further, mean ambulatory morning BP measurements in the RDN treated group were reduced by 7.3±19.6 mm Hg (p<0.001; baseline of 161.2±17.2 mm Hg, p=0.24), whereas they were not significantly reduced (−3.2±21.0 mm Hg; p=0.046) from baseline (160.3±19.2 mm Hg, p=0.579) in the blind control+control group 6 months post-neuromodulation. These findings suggest that patients treated with renal neuromodulation will have decreased ambulatory night-time systolic BP and decreased MSBP which will reduce the patient's likelihood (e.g., lower level of risk) of developing, progressing or worsening cardiovascular disease.

Example 7

Example 6 describes a method for treating human patients diagnosed with hypertension with renal neuromodulation and anticipated outcomes of such treatment. In this example, human patients diagnosed with hypertension will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming a plurality of spaced-apart lesions at the distal segment of the renal artery and within a distance of approximately 6 mm proximal to the branch point within the renal artery using the Symplicity Spyral™ catheter, commercially available from Medtronic, Inc. For example, a first (e.g., most distal) lesion can be formed about 5-6 mm proximal from the bifurcation. Other multi-electrode, spiral/helical-shaped catheters for forming multiple lesions along the length of the vessel are also contemplated for these methods. For patients undergoing main artery treatment at a central segment of the main renal artery, the Symplicity Spyral™ catheter can be used to form a plurality of spaced-apart lesions (e.g., about 2 lesions to about 4 lesions) in a spiral/helical pattern along the central segment of the main renal artery. The catheter may also be moved proximally and/or distally to form multiple sets of lesions during a procedure.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can also be performed using the multi-electrode Symplicity Spyral™ catheter. Other multi-electrode, spiral/helical-shaped catheters having a tighter spiral/helix (e.g., smaller pitch) for forming multiple lesions close in proximity along the length of the vessel are contemplated for these methods.

In a particular example, a method for efficaciously neuromodulating renal nerve tissue in a human patient can include advancing a multi-electrode Symplicity Spyral™ catheter to a first renal artery branch vessel approximately 6 mm distal to the bifurcation. Following retraction of a guidewire and/or straightening sheath, the Symplicity Spyral™ catheter can transform to a spiral/helically-shaped configuration that accommodates the inner diameter of a typical renal artery and/or the branches of the renal artery (e.g., about 2-10 mm), placing the electrodes (e.g., 4 electrodes) in contact with the vessel wall. A first (e.g., most distal) lesion can be formed about 5-6 mm distal to the bifurcation. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment locations (e.g., locations along the main renal vessel, locations at or near the bifurcation, etc.). Other methods can include advancing a multi-electrode Symplicity Spyral™ catheter to a first renal artery branch vessel approximately 10 mm distal to the bifurcation, with a first (e.g., most distal) lesion formed about 9-10 mm distal to the bifurcation.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with hypertension or having an increased risk of developing severe or resistant hypertension (e.g., a predisposition, having one or more biomarkers suggesting an increased likelihood, genetic/epigenetic factors, etc.) or having prehypertension and having one or more measurable risk factors, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20/%, about 30%/a, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial improvement in one or more measurable physiological parameters corresponding to an incidence of hypertension, and/or a severity of hypertension in the patient.

VII. FURTHER EXAMPLES

1. A method for treating hypertension, the method comprising:
    selecting a human patient having a baseline systolic blood pressure of at least approximately 150 mm Hg and a baseline 24-hour heart rate of at least approximately 73 beats per minute (bpm);
    intravascularly delivering an energy delivery element to a renal artery of the selected patient; and
    modulating a renal nerve along the renal artery by delivering energy from the energy delivery element positioned along a wall of the renal artery,
    wherein the selected patient achieves a greater decrease in blood pressure following treatment than a human patient having a baseline systolic blood pressure of at least approximately 150 mm Hg and a baseline 24-hour heart rate of less than approximately 73 bpm following a comparable treatment.

2. The method of example 1, wherein the selected patient achieves a greater decrease in 24-hour heart rate following treatment than the human patient having a baseline 24-hour heart rate of less than approximately 73 bpm following the comparable treatment.

3. The method of example 1 or example 2, wherein the selected patient achieves a decrease in systolic blood pressure of at least approximately 3 mm Hg greater than the human patient having a baseline 24-hour heart rate of less than approximately 73 bpm following the comparable treatment.

4. The method of any one of examples 1-3, wherein the selected patient has a baseline systolic blood pressure of less than approximately 180 mm Hg, less than approximately 170 mm Hg, less than approximately 165 mm Hg, less than approximately 160 mm Hg, less than approximately 155 mm Hg, less than approximately 150 mm Hg, or less than approximately 145 mm Hg.

5. The method of any one of examples 1-4, wherein the selected patient has a diastolic blood pressure of at least approximately 90 mm Hg.

6. The method of any one of examples 1-5, wherein the selected patient is not taking a beta-blocker.

7. The method of any one of examples 1-6, wherein the selected patient is not taking anti-hypertensive medication.

8. The method of any one of examples 1-7, wherein delivering energy from the energy delivery element comprises delivering RF energy to the wall of the renal artery in a spiral pattern along the renal artery.

9. The method of any one of examples 1-8, wherein the 24-hour heart rate is measured by an ambulatory blood pressure monitor.

10. The method of any one of examples 1-9, wherein following the treatment, the selected patient achieves a greater reduction in average morning heart rate than a blinded control group.

11. The method of any one of examples 1-10, wherein following the treatment, the selected patient achieves a greater reduction in average peak night-time heart rate than a blinded control group.

12. The method of any one of examples 1-11, wherein following the treatment, the selected patient achieves a greater reduction in minimum morning heart rate than a blinded control group.

13. The method of any one of examples 1-12, wherein following the treatment, the selected patient achieves a greater reduction in minimum moving peak morning heart rate than a blinded control group.

14. The method of any one of examples 1-13, wherein following the treatment, the selected patient achieves at least one of—
- a greater reduction in average morning heart rate,
- a greater reduction in average peak night-time heart rate,
- a greater reduction in minimum morning heart rate, and
- a greater reduction in minimum moving peak morning heart rate, than the human patient having a baseline systolic blood pressure of at least approximately 150 mm Hg and a baseline 24-hour heart rate of less than approximately 73 bpm following the comparable treatment.

15. The method of any one of examples 1-14, wherein following the treatment, the selected patient achieves a greater reduction in at least one of peak morning heart rate and average morning heart rate surge than the human patient having a baseline systolic blood pressure of at least approximately 150 mm Hg and a baseline 24-hour heart rate of less than approximately 73 bpm following the comparable treatment.

16. The method of any one of examples 1-15, wherein following the treatment, the selected patient achieves a greater reduction in average morning systolic blood pressure that the human patient having a baseline systolic blood pressure of at least approximately 150 mm Hg and a baseline 24-hour heart rate of less than approximately 73 bpm following the comparable treatment.

17. The method of any one of examples 1-16, wherein following the treatment, the selected patient achieves a greater reduction in one or more of—
- average daytime systolic blood pressure,
- average daytime diastolic blood pressure,
- average night-time systolic blood pressure, and
- average night-time diastolic blood pressure, than the human patient having a baseline systolic blood pressure of at least approximately 150 mm Hg and a baseline 24-hour heart rate of less than approximately 73 bpm following the comparable treatment.

18. A method of treating a hypertensive patient, the method comprising:
- selecting a hypertensive patient having a 24-hour heart rate at or above a median heart rate for a population of hypertensive patients;
- intravascularly positioning a neuromodulation assembly within a renal blood vessel of the patient and adjacent to neural fibers innervating a kidney of the patient; and
- partially inhibiting sympathetic neural activity in the neural fibers of the patient via the neuromodulation assembly,
- wherein partially inhibiting sympathetic neural activity results in a reduction in blood pressure in the patient greater than a comparable patient having a 24-hour heart rate below the median heart rate.

19. The method of example 18, wherein the patient has an office systolic blood pressure of at least approximately 140 mm Hg or at least approximately 150 mm Hg.

20. The method of example 18 or example 19, wherein the patient has an office diastolic blood pressure of at least approximately 90 mm Hg.

21. The method of any of examples 18-20, wherein the patient has a mean 24-hour ambulatory systolic blood pressure of between at least approximately 140 mm Hg and approximately 170 mm Hg or between at least approximately 140 mm Hg and approximately 159 mm Hg.

22. The method of any one of examples 18-21, wherein the mean 24-hour heart rate for the population of hypertensive patients is approximately 70 bpm, 71 bpm, 72 bpm, 73, bpm, 73.5 bpm, 74 bpm, or 75 bpm.

23. The method of any one of examples 18-22, wherein neither the patient nor the comparable patient is taking a beta-blocker.

24. The method of any one of examples 18-23, wherein neither the patient nor the comparable is taking anti-hypertensive medication.

25. The method of any one of examples 18-24, wherein following the treatment, the patient achieves at least one of—
- a greater reduction in average morning heart rate,
- a greater reduction in average peak night-time heart rate,
- a greater reduction in minimum morning heart rate, and
- a greater reduction in minimum moving peak morning heart rate, than the comparable patient following treatment.

26. The method of any one of examples 18-25, wherein following the treatment, the patient achieves a greater reduction in at least one of peak morning heart rate and average morning heart rate surge than the comparable patient following treatment.

27. The method of any one of examples 18-26, wherein following the treatment, the patient achieves a greater reduction in average morning systolic blood pressure than the comparable patient following treatment.

28. The method of any one of examples 18-27, wherein within 3 months following the treatment, the patient achieves a greater reduction in one or more of—
- average daytime systolic blood pressure,
- average daytime diastolic blood pressure,
- average night-time systolic blood pressure, and
- average night-time diastolic blood pressure, than the comparable patient within 3 months following treatment.

29. The method of any one of examples 18-28, wherein the patient achieves a decrease in average 24-hour systolic blood pressure of at least approximately 3 mm Hg greater than the comparable patient following treatment.

30. The method of any one of examples 18-29, wherein the patient achieves a decrease in average 24-hour systolic blood pressure of at least approximately 4 mm Hg greater than the comparable patient following treatment.

31. The method of any one of examples 18-30, wherein the patient achieves one or more of—
- a decrease in average daytime systolic blood pressure of at least approximately 3 mm Hg greater than the comparable patient following treatment,
- a decrease in average daytime diastolic blood pressure of at least approximately 3 mm Hg greater than the comparable patient following treatment,
- a decrease in average night-time systolic blood pressure of at least approximately 8 mm Hg greater than the comparable patient following treatment, and
- a decrease in average night-time diastolic blood pressure of at least approximately 4 mm Hg greater than the comparable patient following treatment.

32. The method of any one of examples 18-31, wherein the patient achieves one or more of—
- a decrease in average morning systolic blood pressure of at least approximately 10 mm Hg greater than the comparable patient following treatment,
- a decrease in maximum morning systolic blood pressure of at least approximately 2 mm Hg greater than the comparable patient following treatment, and a decrease in minimum morning systolic blood pressure of at least approximately 4 mm Hg greater than the comparable patient following treatment.

33. The method of any one of examples 18-32, wherein the patient achieves a decrease in systolic blood pressure of at least approximately 3 mm Hg greater than the comparable patient 3 months following treatment.

34. The method of any one of examples 18-33, wherein the renal blood vessel is a renal artery having a diameter of between about 2 mm and about 10 mm.

35. The method of any one of examples 18-34, wherein inhibiting sympathetic neural activity in the neural fibers of the patient via the neuromodulation assembly includes delivering at least one of radio frequency energy, ultrasound energy, high intensity ultrasound energy, laser energy, and microwave energy via the neuromodulation assembly to the neural fibers.

36. The method of any one of examples 18-35, wherein inhibiting sympathetic neural activity in the neural fibers further results in reducing an incidence of one or more of cardiovascular disease, incident heart failure, and cardiovascular morbidity in the patient.

37. The method of any one of examples 18-36, wherein the patient is diagnosed with mild hypertension.

VIII. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for treating hypertension, the method comprising:
    selecting a human patient having a baseline systolic blood pressure of at least approximately 150 mm Hg and a baseline 24-hour heart rate at or above a median heart rate for a population of hypertensive patients;
    intravascularly delivering an energy delivery element to a renal artery of the selected patient; and
    modulating a renal nerve along the renal artery by delivering energy from the energy delivery element positioned along a wall of the renal artery,
    wherein the selected patient achieves a greater decrease in blood pressure following treatment than a human patient achieving an average decrease in blood pressure of a subpopulation of hypertensive patients having a baseline systolic blood pressure of at least approximately 150 mm Hg and a baseline 24-hour heart rate of less than the median heart rate for the population of hypertensive patients following a comparable treatment of intravascularly delivering an energy delivery element to a renal artery of the human patient and modulating a renal nerve along the renal artery of the human patient by delivering energy from the energy delivery element, and
    wherein the selected patient and the human patient are not taking a beta blocker.

2. The method of claim 1, wherein the selected patient achieves a greater decrease in 24-hour heart rate following treatment than the human patient achieving the average decrease in blood pressure of the subpopulation of hypertensive patients following the comparable treatment.

3. The method of claim 1, wherein the selected patient achieves a decrease in systolic blood pressure of at least approximately 3 mm Hg greater than the human patient achieving the average decrease in blood pressure of the subpopulation of hypertensive patients following the comparable treatment.

4. The method of claim 1, wherein the selected patient has at least one of:
    a baseline systolic blood pressure of less than approximately 160 mm Hg, or
    a diastolic blood pressure of at least approximately 90 mm Hg.

5. The method of claim 1, wherein delivering energy from the energy delivery element comprises delivering RF energy to the wall of the renal artery in a spiral pattern along the renal artery.

6. The method of claim 1, wherein following the treatment, the selected patient achieves at least one of:
    a greater reduction in average morning heart rate,
    a greater reduction in average peak night-time heart rate,
    a greater reduction in minimum morning heart rate, or
    a greater reduction in minimum moving peak morning heart rate,
than the human patient achieving the average decrease in blood pressure of the subpopulation of hypertensive patients following the comparable treatment.

7. The method of claim 1, wherein following the treatment, the selected patient achieves a greater reduction in at least one of peak morning heart rate or average morning heart rate surge than the human patient achieving the average decrease in blood pressure of the subpopulation of hypertensive patients following the comparable treatment.

8. The method of claim 1, wherein following the treatment, the selected patient achieves a greater reduction in one or more of:
   average morning systolic blood pressure,
   average daytime systolic blood pressure,
   average daytime diastolic blood pressure,
   average night-time systolic blood pressure, or
   average night-time diastolic blood pressure,
than the human patient achieving the average decrease in blood pressure of the subpopulation of hypertensive patients following the comparable treatment.

9. The method of claim 1,
   wherein the population of hypertensive patients comprises one of:
      a general population of hypertensive patients, or
      a population of hypertensive patients having a same biological sex and an age within 10 years of the selected patient.

10. A method of treating a hypertensive patient, the method comprising:
   selecting the hypertensive patient having a 24-hour heart rate at or above a median heart rate for a population of hypertensive patients;
   intravascularly positioning a neuromodulation assembly within a renal blood vessel of the selected patient and adjacent to neural fibers innervating a kidney of the patient; and
   partially inhibiting sympathetic neural activity in the neural fibers of the selected patient via the neuromodulation assembly,
   wherein partially inhibiting sympathetic neural activity results in a reduction in blood pressure in the selected patient greater than a comparable patient achieving an average reduction in blood pressure of a subpopulation of hypertensive patients having a 24-hour heart rate below the median heart rate, and
   wherein neither the selected patient nor the comparable patient is taking anti-hypertensive medication.

11. The method of claim 10, wherein the selected patient has an office systolic blood pressure of at least approximately 150 mm Hg and an office diastolic blood pressure of at least approximately 90 mm Hg.

12. The method of claim 10, wherein the selected patient has a mean 24-hour ambulatory systolic blood pressure of approximately 140 mm Hg to approximately 155 mm Hg.

13. The method of claim 10, wherein the 24-hour heart rate is measured by an ambulatory blood pressure monitor, and wherein the median 24-hour heart rate for the population of hypertensive patients is approximately 70 bpm to approximately 75 bpm.

14. The method of claim 10, wherein following the treatment, the selected patient achieves at least one of:
   a greater reduction in peak morning heart rate,
   a greater reduction in average morning heart rate surge,
   a greater reduction in average morning heart rate,
   a greater reduction in average peak night-time heart rate,
   a greater reduction in minimum morning heart rate, or
   a greater reduction in minimum moving peak morning heart rate, than the comparable patient following treatment.

15. The method of claim 10, wherein within 3 months following the treatment, the selected patient achieves a greater reduction in one or more of:
   average morning systolic blood pressure,
   average daytime systolic blood pressure,
   average daytime diastolic blood pressure,
   average night-time systolic blood pressure, or
   average night-time diastolic blood pressure,
than the comparable patient within 3 months following treatment.

16. The method of claim 10, wherein the selected patient achieves a decrease in average 24-hour systolic blood pressure of at least approximately 3 mm Hg greater than the comparable patient following treatment.

17. The method of claim 10, wherein the selected patient achieves one or more of:
   a decrease in office systolic blood pressure of at least approximately 3 mm Hg greater than the comparable patient 3 months following treatment
   a decrease in average daytime systolic blood pressure of at least approximately 3 mm Hg greater than the comparable patient 3 months following treatment,
   a decrease in average daytime diastolic blood pressure of at least approximately 3 mm Hg greater than the comparable patient 3 months following treatment,
   a decrease in average night-time systolic blood pressure of at least approximately 8 mm Hg greater than the comparable patient 3 months following treatment, or
   a decrease in average night-time diastolic blood pressure of at least approximately 4 mm Hg greater than the comparable patient 3 months following treatment.

18. The method of claim 10, wherein the selected patient achieves one or more of:
   a decrease in average morning systolic blood pressure of at least approximately 10 mm Hg greater than the comparable patient following treatment,
   a decrease in maximum morning systolic blood pressure of at least approximately 2 mm Hg greater than the comparable patient following treatment, or
   a decrease in minimum morning systolic blood pressure of at least approximately 4 mm Hg greater than the comparable patient following treatment.

19. The method of claim 10, wherein inhibiting sympathetic neural activity in the neural fibers further results in reducing an incidence of one or more of cardiovascular disease, incident heart failure, or cardiovascular morbidity in the selected patient.

20. A method for treating hypertension, the method comprising:
   selecting a human patient having a baseline systolic blood pressure of at least approximately 150 mm Hg and a baseline 24-hour heart rate at or above a median heart rate for a population of hypertensive patients;
   intravascularly delivering an energy delivery element to a renal artery of the selected patient; and
   modulating a renal nerve along the renal artery by delivering energy from the energy delivery element positioned along a wall of the renal artery,
   wherein the selected patient achieves a greater decrease in blood pressure following treatment than a human patient achieving an average decrease in blood pressure of a subpopulation of hypertensive patients having a baseline systolic blood pressure of at least approximately 150 mm Hg and a baseline 24-hour heart rate of less than the median heart rate for the population of hypertensive patients following a comparable treatment of intravascularly delivering an energy delivery element to a renal artery of the human patient and modulating a renal nerve along the renal artery of the human patient by delivering energy from the energy delivery element, and wherein following the treatment, the selected patient achieves a greater reduction in at least one of:
average morning heart rate,
average peak night-time heart rate,
minimum morning heart rate, or
minimum moving peak morning heart rate,
peak morning heart rate,
average morning heart rate surge,
average morning systolic blood pressure,
average daytime systolic blood pressure,
average daytime diastolic blood pressure,
average night-time systolic blood pressure, or
average night-time diastolic blood pressure
than the human patient achieving the average decrease in blood pressure of the subpopulation of hypertensive patients following the comparable treatment.

* * * * *